(12) United States Patent
Bhaskar et al.

(10) Patent No.: US 8,257,708 B2
(45) Date of Patent: *Sep. 4, 2012

(54) ANTIBODIES AGAINST CANCER ANTIGEN TMEFF2 AND USES THEREOF

(75) Inventors: Vinay Bhaskar, San Francisco, CA (US); Agustin De La Calle, Planegg (DE); Debbie Law, San Francisco, CA (US); Ingrid Caras, San Francisco, CA (US); Vanitha Ramakrishnan, Belmont, CA (US); Richard Murray, Cupertino, CA (US); Daniel Afar, Fremont, CA (US); David Powers, Fairfax, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/892,725

(22) Filed: Sep. 28, 2010

(65) Prior Publication Data

US 2011/0038864 A1 Feb. 17, 2011

Related U.S. Application Data

(60) Continuation of application No. 11/837,337, filed on Aug. 10, 2007, now Pat. No. 7,824,678, which is a division of application No. 10/383,447, filed on Mar. 7, 2003, now Pat. No. 7,288,248.

(60) Provisional application No. 60/362,837, filed on Mar. 8, 2002, provisional application No. 60/436,812, filed on Dec. 27, 2002.

(51) Int. Cl.
*A61K 39/395* (2006.01)
*A61P 35/00* (2006.01)
*C07K 16/22* (2006.01)

(52) U.S. Cl. ............... 424/133.1; 424/145.1; 424/158.1; 424/178.1; 424/183.1; 530/387.1; 530/388.24; 530/389.2; 530/391.3

(58) Field of Classification Search .................. 424/133, 424/1, 145.1, 158.1, 178.1, 183.1; 530/387.1, 530/388.24, 389.2, 391.2

See application file for complete search history.

(56) References Cited

U.S. PATENT DOCUMENTS

| 7,288,248 B2 * | 10/2007 | Bhaskar et al. ............ 424/130.1 |
| 7,674,883 B2 * | 3/2010 | Bhaskar et al. ............ 530/387.1 |
| 7,824,678 B2 | 11/2010 | Bhaskar et al. | |
| 2004/0096392 A1 | 5/2004 | Bhaskar et al. | |

OTHER PUBLICATIONS

Voskoglou-Nomikos (Clin. Can. Res. 9:4227-4239 (2003).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
ATCC website search (TMEFF2#19 and ATCC Accession No. PTA-4127; Jul. 21, 2011, pp. 1-2).*
Agus et al., "Response of Prostate Cancer to Anti-Her-2/neu Antibody in Androgen-dependent and—independent Human Xenograft Models", Cancer Research, 59(19): 4761-4 (1999).
Harlow et al., "Antibodies: A Laboratory Manual", Cold Spring Harbor Laboratory, NY 1988, p. 141-142.
Rudikoff et al., "Single amino acid substitution altering antigen-binding specificity" Proc. Natl. Acad. Sci, USA 1982 vol. 79 pp. 1979-1983.
Janeway et al., Immunobiology 5, 2001, pp. 100-101.
Uchida et al., "A novel epidermal growth factor-like molecule containing two follistatin modules stimulates tyrosine phosphorylation of erbB-4 in MKN28 gastric cancer cells", Biochemical and Biophysical Research Comm., vol. 266, pp. 593-602 (1999).
MacCallum et al., "Antibody-antigen interactions: contact analysis and binding site topography", J. Mol. Biol., 262:732-745 (1996).
Gylnne-Jones et al., "TenB2, A protecoglycan identified in prostate cancer that is associated with disease progression and androgen independence", Int. J. Cancer, vol. 94, pp. 178-184 (2001).
Ford et al., "Identification of Differentially Expressed Genes Associated with Recurrent Growth of Prostate Cancer", J. Urology, vol. 165, No. 5, Supplement, p. 138 (2001).
Afar et al., "Preclinical validation of anti-TMEFF2-auristatin E-conjugated antibodies in the treatment of prostate cancer", Molecular Cancer Therapeutics, vol. 3, No. 8, pp. 921-932 (2004).
Greenspan et al., "Defining eptiopes: It's not as easy as it seems", Nature Biotechnology, vol. 17, pp. 936-937 (1999).
Bowie et al., "Deciphering the message in protein sequences: tolerance to amino acid substitutions", Science, vol. 247, No. 4948, pp. 1306-1310 (1990).
Gussow, et al., "Humanization of Monoclonal Antibodies", Methods in Enzymology 203:99-121 (1991).
Gura, T., "Systems for identifying ne drugs are often faulty", Science vol. 278, No. 5340, pp. 1041-1042 (1997).
George et al., "Differential effects of anti-beta2-glycoprotein I antibodies on endothelial cells and on the manifestations of experimental antiphospholipid syndrome," Circulation, 97:900-906 (1998).
Quayle et al., "A truncated isoform of TMEFF2 encodes a secreted protein in prostate cancer cells," Genomics, 87(5):633-637 (2006).
Mariuzza et al., "The structural basis of antigen-antibody recognition," Annu. Rev. Biophys. Chem., 16:139-159 (1987).
Guisti et al., "Somatic diversification of S107 from an antiphosphocholine to an anti-DNA autoantibody is due to a single base change in its heavy chain variable region," Proc. Natl. Acad. Sci. USA 84(9):2926-2930 (1987).
Chien et al.,"Significant structural and functional change of an antigen-bending site by a distant amino acid substitution: Proposal of a structural mechanism," Proc. Natl. Acad. Sci. USA 86(14):5532-5536 (1989).
Caldas et al.,"Humanization of the anti-CD18 antibody 6.7: an unexpected effect of a framework residue in binding to antigen", Mol. Immunol. 39(15):941-952 (2003).
Gery et al., "TMEFF2s an androgen-regulated gene exhibiting antiproliferative effects in prostate cancer cells," Oncogene, 21(31):4739-4746 (2002).
Antunes et al.,"The role of prostate specific membrane antigen and pepsinogen C tissue expression as an adjunctive method to prostate cancer diagnosis," J. Urol. 181(2):594-600 (2009).
Wu, et al., "Humanization of a murine monoclonal antibody by simultaneous optimization of framework and CDR resides", J. Mol. Biol. 294:151-162 (1999).

* cited by examiner

*Primary Examiner* — Lynn Bristol
(74) *Attorney, Agent, or Firm* — Sughrue Mion, PLLC

(57) ABSTRACT

The invention relates to the identification and generation of antibodies that bind to TMEFF2 proteins which are involved in cancer. Further, the invention provides for the use of these antibodies in the treatment of cancer.

21 Claims, No Drawings

SEQUENCE LISTING

<160> NUMBER OF SEQ ID NOS: 34

<210> SEQ ID NO 1
<211> LENGTH: 360
<212> TYPE: DNA
<213> ORGANISM: Mus sp.

<400> SEQUENCE: 1

```
gatgtacaac ttcaggagtc aggacctggc ctcgtgaaac cttctcagtc tctgtctctc      60
acctgctctg tcactggcta ctccatcacc agtggttatt actggagctg gatccggcag     120
```

```
tttccaggaa acaaactgga atggatgggc ttcataagct acgacggttc caataagtat    180
aatccatctc tcaaaaatcg aatctccatc actcgtgaca catctgagaa ccagttttc    240 ctgaacttga gatctgtgac tactgaggac acagcaacat attattgtgc aagaggttta   300
cgacgagggg actattctat ggactactgg ggtcaaggaa cctcagtcac cgtctcctca   360
```

<210> SEQ ID NO 2
<211> LENGTH: 120
<212> TYPE: PRT
<213> ORGANISM: Mus sp.

<400> SEQUENCE: 2

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Ser Trp Ile Arg Gln Phe Pro Gly Asn Lys Leu Glu Trp
        35                  40                  45

Met Gly Phe Ile Ser Tyr Asp Gly Ser Asn Lys Tyr Asn Pro Ser Leu
    50                  55                  60

Lys Asn Arg Ile Ser Ile Thr Arg Asp Thr Ser Glu Asn Gln Phe Phe
65                  70                  75                  80

Leu Asn Leu Arg Ser Val Thr Thr Glu Asp Thr Ala Thr Tyr Tyr Cys
                85                  90                  95

Ala Arg Gly Leu Arg Arg Gly Asp Tyr Ser Met Asp Tyr Trp Gly Gln
            100                 105                 110

Gly Thr Ser Val Thr Val Ser Ser
        115                 120
```

<210> SEQ ID NO 3
<211> LENGTH: 321
<212> TYPE: DNA
<213> ORGANISM: Mus sp.

<400> SEQUENCE: 3

```
gacattgtga tgacccagtc tcaaaaattc atgtccacat cagtaggaga cagtgtcagc    60
atcacctgca aggccagtca gaatgtggtt acagctgtag cctggtatcg acagaaacca   120
ggacaatctc ctaaactact gatttactcg gcatccaatc ggcacactgg agtccctgac   180
cgcttcacag gcagtggatc tgggacagat ttcactctca ccatcaacaa tatgcagtct   240
gaagacctgg cagattattt ctgccagcaa tatagcagct atccgttcac gttcggaggg   300
gggaccaagc tggaaataaa a                                              321
```

<210> SEQ ID NO 4
<211> LENGTH: 107
<212> TYPE: PRT
<213> ORGANISM: Mus sp.

<400> SEQUENCE: 4

```
Asp Ile Val Met Thr Gln Ser Gln Lys Phe Met Ser Thr Ser Val Gly
1               5                   10                  15

Asp Ser Val Ser Ile Thr Cys Lys Ala Ser Gln Asn Val Val Thr Ala
            20                  25                  30

Val Ala Trp Tyr Arg Gln Lys Pro Gly Gln Ser Pro Lys Leu Leu Ile
        35                  40                  45

Tyr Ser Ala Ser Asn Arg His Thr Gly Val Pro Asp Arg Phe Thr Gly
    50                  55                  60
```

```
Ser Gly Ser Gly Thr Asp Phe Thr Leu Thr Ile Asn Asn Met Gln Ser
 65                  70                  75                  80

Glu Asp Leu Ala Asp Tyr Phe Cys Gln Gln Tyr Ser Ser Tyr Pro Phe
                 85                  90                  95

Thr Phe Gly Gly Gly Thr Lys Leu Glu Ile Lys
            100                 105

<210> SEQ ID NO 5
<211> LENGTH: 360
<212> TYPE: DNA
<213> ORGANISM: Mus sp.

<400> SEQUENCE: 5
gaagtgaacc tggtggagtc tgggggaggc ttagtgcagc ctggagggtc cctgaaactc     60
tcctgtgcaa cctctggatt cactttcagt gactattaca tgttctggat cgccagact    120 ccagagaaga ggctgagtg gtcgcatac attagtaatg gtggtggtaa tacctattat     180
tcagacactg taaagggccg attcaccatc tccagagaca atgccaagaa cacccctgtac  240 ctccaaatga gccgtctgaa gtctgaggac acagccatgt attactgtgc aagacgggga   300
ttacgacgag ggggggctat ggactactgg ggtcaaggaa cctcagtcac cgtctcctca   360

<210> SEQ ID NO 6
<211> LENGTH: 120
<212> TYPE: PRT
<213> ORGANISM: Mus sp.

<400> SEQUENCE: 6

Glu Val Asn Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Tyr
                20                  25                  30

Tyr Met Phe Trp Ile Arg Gln Thr Pro Glu Lys Arg Leu Glu Trp Val
            35                  40                  45

Ala Tyr Ile Ser Asn Gly Gly Gly Asn Thr Tyr Tyr Ser Asp Thr Val
        50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ala Arg Arg Gly Leu Arg Arg Gly Gly Ala Met Asp Tyr Trp Gly Gln
            100                 105                 110

Gly Thr Ser Val Thr Val Ser Ser
            115                 120

<210> SEQ ID NO 7
<211> LENGTH: 333
<212> TYPE: DNA
<213> ORGANISM: Mus sp.

<400> SEQUENCE: 7
gacattgttt tgacccaatc tccagcttct ttggctgtgt ctctagggca gagggccacc    60
atctcctgca aggccagcca agtgttgat tacggtggtt atggttatat aaactggtac    120
caacagaaac aggacagcc acccaaactc ctcatctatg ctgcatccaa tctagaatct    180
gggatcccag ccaggtttag tggcagtggg tctgggacag atttcaccct caacatccat   240
cctgtggagg aggaggatgc tgcagtctat tactgtcaac aaagttatgt ggatccattc    300
acgttcggct cggggacaaa gttggaaata atc                                 333
```

<210> SEQ ID NO 8
<211> LENGTH: 111
<212> TYPE: PRT
<213> ORGANISM: Mus sp.

<400> SEQUENCE: 8

```
Asp Ile Val Leu Thr Gln Ser Pro Ala Ser Leu Ala Val Ser Leu Gly
1               5                  10                  15

Gln Arg Ala Thr Ile Ser Cys Lys Ala Ser Gln Ser Val Asp Tyr Gly
            20                  25                  30

Gly Tyr Gly Tyr Ile Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Val Tyr Tyr Cys Gln Gln Ser Tyr
                85                  90                  95

Val Asp Pro Phe Thr Phe Gly Ser Gly Thr Lys Leu Glu Ile Ile
            100                 105                 110
```

<210> SEQ ID NO 9
<211> LENGTH: 336
<212> TYPE: DNA
<213> ORGANISM: Mus sp.

<400> SEQUENCE: 9

```
cagatccagt tggtgcagtc tggacctgag ctgaagaagc ctggagagac agtcaagatc    60
tcctgcaagg cttctgggta taccttcaca aactatggaa tgagctgggt gaagcaggct   120
ccaggaaagg gtttaaagtg gatgggctgg ataaacacct acactggaga gccaacatat   180
gctgatgact caaggggcg gtttgccttc tctttggaaa cctctgccag cactgcctat   240
ttgcagatca caacctcaa aaatgaggac acggctacat atttctgtgg gggtgatgct   300
tactggggcc aagggactct ggtcactgtc tctgca                             336
```

<210> SEQ ID NO 10
<211> LENGTH: 112
<212> TYPE: PRT
<213> ORGANISM: Mus sp.

<400> SEQUENCE: 10

```
Gln Ile Gln Leu Val Gln Ser Gly Pro Glu Leu Lys Lys Pro Gly Glu
1               5                  10                  15

Thr Val Lys Ile Ser Cys Lys Ala Ser Gly Tyr Thr Phe Thr Asn Tyr
            20                  25                  30

Gly Met Ser Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Gly Gly Asp Ala Tyr Trp Gly Gln Gly Thr Leu Val Thr Val Ser Ala
            100                 105                 110
```

```
<210> SEQ ID NO 11
<211> LENGTH: 330
<212> TYPE: DNA
<213> ORGANISM: Mus sp.

<400> SEQUENCE: 11
gacattgtgc tgacacagtc tcctgcttcc ttagctgtat ctctggggca gagggccacc      60
atctcatgca gggccagcaa aagtgtcagt acatctggct atagttatat gcactggtac     120
caacagaaac caggacagcc acccaaactc ctcatctatc ttgcatccaa cctagaatct     180
ggggtccctg ccaggttcag tggcagtggg tctgggacag acttcaccct caacatccat     240
cctgtggagg aggaggatgc tgcaacctat tactgtcagc acagtaggga gcttcggacg     300
ttcggtggag gcaccaaact ggaaatcaaa                                      330

<210> SEQ ID NO 12
<211> LENGTH: 110
<212> TYPE: PRT
<213> ORGANISM: Mus sp.

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Arg Thr Phe Gly Gly Gly Thr Lys Leu Glu Ile Lys
            100                 105                 110

<210> SEQ ID NO 13
<211> LENGTH: 351
<212> TYPE: DNA
<213> ORGANISM: Mus sp.

<400> SEQUENCE: 13
gagatccagc tgcagcagtc tggacctgag ctgatgaagc ctggggcttc agtgaagata      60
tcttgcaagg cttctactta ctcattcact aggtacttca tgcactgggt gaagcagagc     120
catggagaga gccttgagtg gattggatat attgatcctt caatggtgg tactggctac     180 aatcagaaat tcaagggcaa ggccacattg actgtagaca atcttccag cacagcctac     240 atgcatctca gcagcctgac atctgaggac tctgcagtct attactgtgt aacgtatggc     300
tccgactact ttgactattg gggccaaggc accactctca cagtctcctc a              351

<210> SEQ ID NO 14
<211> LENGTH: 117
<212> TYPE: PRT
<213> ORGANISM: Mus sp.

<400> SEQUENCE: 14

Glu Ile Gln Leu Gln Gln Ser Gly Pro Glu Leu Met Lys Pro Gly Ala
1               5                   10                  15

Ser Val Lys Ile Ser Cys Lys Ala Ser Thr Tyr Ser Phe Thr Arg Tyr
```

```
                    20                  25                  30
Phe Met His Trp Val Lys Gln Ser His Gly Glu Ser Leu Glu Trp Ile
         35                  40                  45
Gly Tyr Ile Asp Pro Phe Asn Gly Gly Thr Gly Tyr Asn Gln Lys Phe
     50                  55                  60
Lys Gly Lys Ala Thr Leu Thr Val Asp Lys Ser Ser Thr Ala Tyr
 65                  70                  75                  80
Met His Leu Ser Ser Leu Thr Ser Glu Asp Ser Ala Val Tyr Tyr Cys
                 85                  90                  95
Val Thr Tyr Gly Ser Asp Tyr Phe Asp Tyr Trp Gly Gln Gly Thr Thr
             100                 105                 110
Leu Thr Val Ser Ser
         115

<210> SEQ ID NO 15
<211> LENGTH: 321
<212> TYPE: DNA
<213> ORGANISM: Mus sp.

<400> SEQUENCE: 15
gacattgtga tgacccagcc acaaaaattc atgtccacgt ctgtaggcga cagggtcagt     60
gtcacctgca aggccagtca gaatgtggaa actgatgtag tctggtatca acagaaacct    120
gggcaaccac ctaaagcact gatttactcg gcatcctacc ggcacagtgg agtccctgat    180
cgcttcacag gcagtggatc tgggacaaat ttcactctca ccatcagcac tgtacagtct    240
gaagacttgg cagagtattt ctgtcagcaa tataacaact atccattcac gttcggctcg    300
gggacaaagt tggaaataat a                                              321

<210> SEQ ID NO 16
<211> LENGTH: 107
<212> TYPE: PRT
<213> ORGANISM: Mus sp.

<400> SEQUENCE: 16

Asp Ile Val Met Thr Gln Pro Gln Lys Phe Met Ser Thr Ser Val Gly
  1               5                  10                  15
Asp Arg Val Ser Val Thr Cys Lys Ala Ser Gln Asn Val Glu Thr Asp
             20                  25                  30
Val Val Trp Tyr Gln Gln Lys Pro Gly Gln Pro Pro Lys Ala Leu Ile
         35                  40                  45
Tyr Ser Ala Ser Tyr Arg His Ser Gly Val Pro Asp Arg Phe Thr Gly
     50                  55                  60
Ser Gly Ser Gly Thr Asn Phe Thr Leu Thr Ile Ser Thr Val Gln Ser
 65                  70                  75                  80
Glu Asp Leu Ala Glu Tyr Phe Cys Gln Gln Tyr Asn Asn Tyr Pro Phe
                 85                  90                  95
Thr Phe Gly Ser Gly Thr Lys Leu Glu Ile Ile
            100                 105

<210> SEQ ID NO 17
<211> LENGTH: 336
<212> TYPE: DNA
<213> ORGANISM: Mus sp.

<400> SEQUENCE: 17 cagatcccact tggtgcagtc tggacctgag ctgaagaagc ctggagagac agtcaagatc     60
tcctgcaagg cttctggata taccttcaca aactttgcaa tgaactgggt gaagcaggct    120
```

```
ccaggaaagg gtttcaagtg gatgggctgg ataaacacct acactggaga gccaacatat    180
gctgatgact tcaagggacg gtttgccttc tctttggaaa cctctgtcag tattgcctat    240
ttgcagatca acagcctcaa aaatgaggac acggctacat atttctgttc aaaatttgac    300
tactggggcc aaggcaccac tctcacagtc tcctca                              336
```

<210> SEQ ID NO 18
<211> LENGTH: 112
<212> TYPE: PRT
<213> ORGANISM: Mus sp.

<400> SEQUENCE: 18

```
Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Ala Met Asn Trp Val Lys Gln Ala Pro Gly Lys Gly Phe Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Val Ser Ile Ala Tyr
65                  70                  75                  80

Leu Gln Ile Asn Ser Leu Lys Asn Glu Asp Thr Ala Thr Tyr Phe Cys
                85                  90                  95

Ser Lys Phe Asp Tyr Trp Gly Gln Gly Thr Thr Leu Thr Val Ser Ser
            100                 105                 110
```

<210> SEQ ID NO 19
<211> LENGTH: 324
<212> TYPE: DNA
<213> ORGANISM: Mus sp.

<400> SEQUENCE: 19

```
gacatccaga tgactcagtc tccagcctcc ctatatgcat ctgtgggaga aactgtcacc     60
atcacatgtc gagcaagtga gaatatttac agttatttag catggtttca gcagaaacag    120
ggaaaatctc ctcacctcct ggtctataat gcaaaaacct tagcagcagg tgtgccatca    180
aggttcagtg gcagtggatc aggcacacag ttttctctga agatcaccag cctgcagcct    240
gaagattttg ggagttatta ctgtcaacat cattatggta ctcccacgtg acgttcggt     300 ggaggcacca agctggaaat caaa                                            324
```

<210> SEQ ID NO 20
<211> LENGTH: 108
<212> TYPE: PRT
<213> ORGANISM: Mus sp.

<400> SEQUENCE: 20

```
Asp Ile Gln Met Thr Gln Ser Pro Ala Ser Leu Tyr Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Phe Gln Gln Lys Gln Gly Lys Ser Pro His Leu Leu Val
        35                  40                  45

Tyr Asn Ala Lys Thr Leu Ala Ala Gly Val Pro Ser Arg Phe Ser Gly
    50                  55                  60

Ser Gly Ser Gly Thr Gln Phe Ser Leu Lys Ile Thr Ser Leu Gln Pro
65                  70                  75                  80
```

Glu Asp Phe Gly Ser Tyr Tyr Cys Gln His His Tyr Gly Thr Pro Thr
            85                  90                  95

Trp Thr Phe Gly Gly Gly Thr Lys Leu Glu Ile Lys
            100                 105

<210> SEQ ID NO 21
<211> LENGTH: 360
<212> TYPE: DNA
<213> ORGANISM: Artificial
<220> FEATURE:
<223> OTHER INFORMATION: Humanized antibody

<400> SEQUENCE: 21

```
gatgtacaac ttcaggagtc aggacctggc ctcgtgaaac cttctgagac cctgtctctc      60
acctgcgcag tcactggcta ctccatcacc agtggttatt actggagctg gatccggcag     120
tttccaggaa agaaactgga atggatgggc ttcataagct acgacggttc caataagtat     180
aatccatctc tcaaaaatcg aatctccatc actcgtgaca catctgagaa ccagttttc      240 ctgaagttgt cttctgtgac tgcagcagac acagcaacat attattgtgc aagaggttta    300
cgacgagggg actattctat ggactactgg ggtcaaggaa ccctggtcac cgtctcctca    360
```

<210> SEQ ID NO 22
<211> LENGTH: 120
<212> TYPE: PRT
<213> ORGANISM: Artificial
<220> FEATURE:
<223> OTHER INFORMATION: Humanized antibody

<400> SEQUENCE: 22

Asp Val Gln Leu Gln Glu Ser Gly Pro Gly Leu Val Lys Pro Ser Glu
1               5                   10                  15

Thr Leu Ser Leu Thr Cys Ala Val Thr Gly Tyr Ser Ile Thr Ser Gly
            20                  25                  30

Tyr Tyr Trp Ser Trp Ile Arg Gln Phe Pro Gly Lys Lys Leu Glu Trp
            35                  40                  45

Met Gly Phe Ile Ser Tyr Asp Gly Ser Asn Lys Tyr Asn Pro Ser Leu
    50                  55                  60

Lys Asn Arg Ile Ser Ile Thr Arg Asp Thr Ser Glu Asn Gln Phe Phe
65                  70                  75                  80

Leu Lys Leu Ser Ser Val Thr Ala Ala Asp Thr Ala Thr Tyr Tyr Cys
            85                  90                  95

Ala Arg Gly Leu Arg Arg Gly Asp Tyr Ser Met Asp Tyr Trp Gly Gln
            100                 105                 110

Gly Thr Leu Val Thr Val Ser Ser
        115                 120

<210> SEQ ID NO 23
<211> LENGTH: 360
<212> TYPE: DNA
<213> ORGANISM: Artificial
<220> FEATURE:
<223> OTHER INFORMATION: Humanized antibody

<400> SEQUENCE: 23

```
gatgtacaac ttcaggagtc aggacctggc ctcgtgaaac cttctgagac cctgtctctc      60
acctgcgcag tcactggcta ctccatcacc agtggttatt actggagctg gatccggcag     120
cctccaggaa agggcctgga atggatgggc ttcataagct acgacggttc caataagtat     180
aatccatctc tcaaaaatcg aatctccatc actcgtgaca catctgagaa ccagttttc      240
```

```
ctgaagttgt cttctgtgac tgcagcagac acagcagtct attattgtgc aagaggttta      300
cgacgagggg actattctat ggactactgg ggtcaaggaa ccctggtcac cgtctcctca      360
```

<210> SEQ ID NO 24
<211> LENGTH: 120
<212> TYPE: PRT
<213> ORGANISM: Artificial
<220> FEATURE:
<223> OTHER INFORMATION: Humanized antibody

<400> SEQUENCE: 24

```
Asp Val Gln Leu Gln Glu Ser Gly Pro Gly Leu Val Lys Pro Ser Glu
1               5                   10                  15

Thr Leu Ser Leu Thr Cys Ala Val Thr Gly Tyr Ser Ile Thr Ser Gly
            20                  25                  30

Tyr Tyr Trp Ser Trp Ile Arg Gln Pro Pro Gly Lys Gly Leu Glu Trp
        35                  40                  45

Met Gly Phe Ile Ser Tyr Asp Gly Ser Asn Lys Tyr Asn Pro Ser Leu
    50                  55                  60

Lys Asn Arg Ile Ser Ile Thr Arg Asp Thr Ser Glu Asn Gln Phe Phe
65                  70                  75                  80

Leu Lys Leu Ser Ser Val Thr Ala Ala Asp Thr Ala Val Tyr Tyr Cys
                85                  90                  95

Ala Arg Gly Leu Arg Arg Gly Asp Tyr Ser Met Asp Tyr Trp Gly Gln
            100                 105                 110

Gly Thr Leu Val Thr Val Ser Ser
        115                 120
```

<210> SEQ ID NO 25
<211> LENGTH: 360
<212> TYPE: DNA
<213> ORGANISM: Artificial
<220> FEATURE:
<223> OTHER INFORMATION: Humanized antibody

<400> SEQUENCE: 25

```
gatgtacaac ttcaggagtc aggacctggc ctcgtgaaac cttctgagac cctgtctctc      60
acctgcgcag tcagcggcta ctccatcacc agtggttatt actggagctg gatccggcag     120
cctccaggaa agggcctgga atggatgggc ttcataagct acgacggttc caataagtat     180
aatccatctc tcaaaaatcg aatcaccatc tcccgtgaca catctaagaa ccagttttcc     240
ctgaagttgt cttctgtgac tgcagcagac acagcagtct attattgtgc aagaggttta     300
cgacgagggg actattctat ggactactgg ggtcaaggaa ccctggtcac cgtctcctca     360
```

<210> SEQ ID NO 26
<211> LENGTH: 120
<212> TYPE: PRT
<213> ORGANISM: Artificial
<220> FEATURE:
<223> OTHER INFORMATION: Humanized antibody

<400> SEQUENCE: 26

```
Asp Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Tyr Trp Ser Trp Ile Arg Gln Pro Pro Gly Lys Gly Leu Glu Trp
        35                  40                  45
```

```
Met Gly Phe Ile Ser Tyr Asp Gly Ser Asn Lys Tyr Asn Pro Ser Leu
        50                  55                  60

Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Arg Arg Gly Asp Tyr Ser Met Asp Tyr Trp Gly Gln
                100                 105                 110

Gly Thr Leu Val Thr Val Ser Ser
            115                 120
```

<210> SEQ ID NO 27
<211> LENGTH: 360
<212> TYPE: DNA
<213> ORGANISM: Artificial
<220> FEATURE:
<223> OTHER INFORMATION: Humanized antibody

<400> SEQUENCE: 27

```
gatgtacaac ttcaggagtc aggacctggc ctcgtgaaac cttctgagac cctgtctctc      60
acctgcgcag tcagcggcta ctccatcacc agtggttatt actggagctg gatccggcag     120
tttccaggaa agaaactgga atggatgggc ttcataagct acgacggttc aataagtat      180 aatccatctc tcaaaaatcg aatcaccatc tcccgtgaca catctaagaa ccagttttcc     240
ctgaagttgt cttctgtgac tgcagcagac acagcaacat attattgtgc aagaggttta     300
cgacgagggg actattctat ggactactgg ggtcaaggaa ccctggtcac cgtctcctca     360
```

<210> SEQ ID NO 28
<211> LENGTH: 120
<212> TYPE: PRT
<213> ORGANISM: Artificial
<220> FEATURE:
<223> OTHER INFORMATION: Humanized antibody

<400> SEQUENCE: 28

```
Asp Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Gly
             20                  25                  30

Tyr Tyr Trp Ser Trp Ile Arg Gln Phe Pro Gly Lys Lys Leu Glu Trp
         35                  40                  45

Met Gly Phe Ile Ser Tyr Asp Gly Ser Asn Lys Tyr Asn Pro Ser Leu
     50                  55                  60

Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Thr Tyr Tyr Cys
                 85                  90                  95

Ala Arg Gly Leu Arg Arg Gly Asp Tyr Ser Met Asp Tyr Trp Gly Gln
                100                 105                 110

Gly Thr Leu Val Thr Val Ser Ser
            115                 120
```

<210> SEQ ID NO 29
<211> LENGTH: 324
<212> TYPE: DNA
<213> ORGANISM: Artificial
<220> FEATURE:
<223> OTHER INFORMATION: Humanized antibody

<400> SEQUENCE: 29

```
gacattcaga tgacccagtc tcaatctagt atgtccacat cagtaggaga ccgagtcacc      60
atcacctgca aggccagtca gaatgtggtt acagctgtag cctggtatcg acagaaacca     120
ggaaagtctc ctaaactact gatttactcg gcatccaatc ggcacactgg agtccctagt     180
cgcttctctg gcagtggatc tgggacagat ttcactctca ccatctctag catgcagcct     240
gaagacttcg cagattattt ctgccagcaa tatagcagct atccgttcac gttcggaggg     300
gggaccaagc tcgagatcaa acgg                                            324
```

<210> SEQ ID NO 30
<211> LENGTH: 108
<212> TYPE: PRT
<213> ORGANISM: Artificial
<220> FEATURE:
<223> OTHER INFORMATION: Humanized antibody

<400> SEQUENCE: 30

```
Asp Ile Gln Met Thr Gln Ser Gln Ser Ser Met Ser Thr Ser Val Gly
1               5                   10                  15

Asp Arg Val Thr Ile Thr Cys Lys Ala Ser Gln Asn Val Val Thr Ala
            20                  25                  30

Val Ala Trp Tyr Arg Gln Lys Pro Gly Lys Ser Pro Lys Leu Leu Ile
        35                  40                  45

Tyr Ser Ala Ser Asn Arg His Thr Gly Val Pro Ser Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Asp Tyr Phe Cys Gln Gln Tyr Ser Ser Tyr Pro Phe
                85                  90                  95

Thr Phe Gly Gly Gly Thr Lys Leu Glu Ile Lys Arg
            100                 105
```

<210> SEQ ID NO 31
<211> LENGTH: 324
<212> TYPE: DNA
<213> ORGANISM: Artificial
<220> FEATURE:
<223> OTHER INFORMATION: Humanized antibody

<400> SEQUENCE: 31

```
gacattcaga tgacccagtc tccatctagt ctgtccgctt cagtaggaga ccgagtcacc      60
atcacctgca aggccagtca gaatgtggtt acagctgtag cctggtatcg acagaaacca     120
ggaaagtctc ctaaactact gatttactcg gcatccaatc ggcacactgg agtccctagt     180
cgcttctctg gcagtggatc tgggacagat ttcactctca ccatctctag cctgcagcct     240
gaagacttcg cagattattt ctgccagcaa tatagcagct atccgttcac gttcggaggg     300
gggaccaagg tcgagatcaa acgg                                            324
```

<210> SEQ ID NO 32
<211> LENGTH: 108
<212> TYPE: PRT
<213> ORGANISM: Artificial
<220> FEATURE:
<223> OTHER INFORMATION: Humanized antibody

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Ala
```

```
                    20                  25                  30

Val Ala Trp Tyr Arg Gln Lys Pro Gly Lys Ser Pro Lys Leu Leu Ile
            35                  40                  45

Tyr Ser Ala Ser Asn Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Ser Ser Tyr Pro Phe
                85                  90                  95

Thr Phe Gly Gly Gly Thr Lys Val Glu Ile Lys Arg
            100                 105

<210> SEQ ID NO 33
<211> LENGTH: 324
<212> TYPE: DNA
<213> ORGANISM: Artificial
<220> FEATURE:
<223> OTHER INFORMATION: Humanized antibody

<400> SEQUENCE: 33
gacattcaga tgacccagtc tccatctagt ctgtccgctt cagtaggaga ccgagtcacc      60
atcacctgca aggccagtca gaatgtggtt acagctgtag cctggtatca gcagaaacca     120
ggaaaggccc ctaaactact gatttactcg gcatccaatc ggcacactgg agtccctagt     180
cgcttctctg gcagtggatc tgggacagat ttcactctca ccatctctag cctgcagcct     240
gaagacttcg caacctatta ttgccagcaa tatagcagct atccgttcac gttcggaggg     300
gggaccaagg tcgagatcaa acgg                                            324

<210> SEQ ID NO 34
<211> LENGTH: 108
<212> TYPE: PRT
<213> ORGANISM: Artificial
<220> FEATURE:
<223> OTHER INFORMATION: Humanized antibody

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Phe
                85                  90                  95

Thr Phe Gly Gly Gly Thr Lys Val Glu Ile Lys Arg
            100                 105
```

ANTIBODIES AGAINST CANCER ANTIGEN TMEFF2 AND USES THEREOF

CROSS-REFERENCES TO RELATED APPLICATIONS

This application is a continuation of U.S. application Ser. No. 11/837,337, filed Aug. 10, 2007, now U.S. Pat. No. 7,824, 678, which is a divisional under 35 U.S.C. §121 of U.S. application Ser. No. 10/383,447, filed Mar. 7, 2003, now U.S. Pat. No. 7,288,248, which claims priority under 35 U.S.C. §119(e) to U.S. Provisional Application Nos. 60/362,837, filed Mar. 8, 2002, and 60/436,812, filed Dec. 27, 2002, all of which are incorporated herein by reference in their entirety.

FIELD OF THE INVENTION

The invention relates to the identification and generation of antibodies that specifically bind to TMEFF2 proteins that are involved in cancer; and to the use of such antibodies and compositions comprising them in the diagnosis, prognosis and therapy of cancer.

BACKGROUND OF THE INVENTION

Prostate cancer is the most frequently diagnosed cancer and the second leading cause of male cancer death in North America and northern Europe. Early detection of prostate cancer using a serum test for prostate-specific antigen (PSA) has dramatically improved the treatment of the disease (Oesterling, 1992, J. Am. Med. Assoc. 267:2236-2238 and DiVita et al. (1997) *Cancer: Principles and Practices of Oncology*, 5$^{th}$ ed. Lippincott-Raven pub.). Treatment of prostate cancer consists largely of surgical prostatectomy, radiation therapy, androgen ablation therapy and chemotherapy. Although many prostate cancer patients are effectively treated, the current therapies can all induce serious side effects which diminish quality of life. For example, patients who present with metastatic disease are most often treated with androgen-ablation therapy. Chemical or surgical castration has been the primary treatment for symptomatic metastatic prostate cancer for over 50 years. While this testicular androgen deprivation therapy usually results in stabilization or regression of the disease (in 80% of patients), progression of metastatic prostate cancer eventually develops (Panvichian et al., *Cancer Control* 3(6):493-500 (1996); Afrin and Stuart, 1994, J. S. C. Med. Assoc. 90:231-236). Metastatic disease is currently considered incurable. Thus, the primary goals of treatment are to prolong survival and improve quality of life (Rago, *Cancer Control* 5(6):513-521 (1998)).

Clearly, the identification of novel therapeutic targets and diagnostic markers is essential for improving the current treatment of prostate cancer patients. Recent advances in molecular medicine have increased the interest in tumor-specific cell surface antigens that could serve as targets for various immunotherapeutic or small molecule strategies. Antigens suitable for immunotherapeutic strategies should be highly expressed in cancer tissues and ideally not expressed in normal adult tissues. One such antigen is TMEFF2.

The TMEFF2 protein contains 2 follistatin-like domains and a conserved EGF-like domain. The gene encoding the protein was first characterized from a human brain cDNA library (see Uchida, et al. (1999) *Biochem. Biophys. Res. Commun.* 266:593-602), and later isolated from a human fetal brain cDNA library (see Horie, et al. (2000) *Genomics* 67:146-152). See also, e.g., Online Mendelian Inheritance in Man, number 605734; Unigene Cluster Hs.22791; Locus-Link 23671; and other linked sites. TMEFF2 has been referred to as tomoregulin, TR, hyperplastic polyposis gene 1, HPP1, and TENB2. TMEFF2's nucleic acid sequence can be identified by ATCC Accession Nos. AF264150, AB004064, AB017269, and AF179274. TMEFF2's amino acid sequence can be identified by ATCC Accession Nos. AAF91397, BAA90820, BAA87897, and AAD55776. TMEFF2's Uni-Gene Cluster identification number is hs.22791, Locuslink identification number is 23671, and OMIM identification number is 605734.

The gene has also been implicated in certain cancerous conditions. Young, et al. (2001) *Proc. Nat'l Acad. Sci. USA* 98:265-270 reported expression in colorectal polyps. Glynne-Jones, et al. (2001) *Int. J. Cancer* 94:178-184 reported it as a marker for prostate cancer.

Treatments such as surgery, radiation therapy, and cryotherapy are potentially curative when the cancer remains localized. Therefore, early detection of cancer is important for a positive prognosis for treatment.

Thus, antibodies that can be used for diagnosis and prognosis and effective treatment of cancer, and including particularly metastatic cancer, would be desirable. Accordingly, provided herein are compositions and methods that can be used in diagnosis, prognosis, and therapy of certain cancers.

SUMMARY OF THE INVENTION

The present invention provides anti-TMEFF2 antibodies that are surprisingly well internalized and are particularly useful for making conjugated antibodies for therapeutic purposes. In some embodiments, the antibodies of the present invention are therapeutically useful in persons diagnosed with cancer and other proliferative conditions, including benign proliferative conditions. In one aspect, the antibodies of the present invention can be used to treat proliferative conditions of the prostate including, e.g., benign prostate hyperplasia and prostate cancer. In another aspect, the antibodies of the present invention can be used to treat malignant and benign proliferative conditions of the brain including, e.g., gliobastomas, oligodendrogliomas, anablastic astrocytomas, meningiomas, medulloblastomas, and neuroblastomas.

In particular, the present invention provides anti-TMEFF2 antibodies that are particularly useful as selective cytotoxic agents for TMEFF2 expressing cells. Without wishing to be bound by theory it is believed that the antibodies of the invention recognize a TMEFF2 epitope that effects an increased internalization, and thus enhanced cell killing, when conjugated to a cytotoxic moiety.

The present invention provides antibodies that competitively inhibit binding of TMEFF2#19 (ATCC Accession No. PTA-4127, deposited on Mar. 6, 2002 with the American Type Culture Collection, 10801 University Blvd., Manassas, Va. 20110-2209) to TMEFF2. In some embodiments the antibodies are further conjugated to an effector component. The effector component can be a label (e.g., a fluorescent label) or can be cytotoxic moiety (e.g., a radioisotope or a cytotoxic chemical). An exemplary cytotoxic chemical is auristatin.

The antibodies of the invention can be whole antibodies or can antibody fragments. In some embodiments the immunoglobulin is a humanized antibody. An exemplary antibody of the invention is TMEFF2#19 (ATCC Accession No. PTA-4127).

The invention also provides pharmaceutical compositions comprising a pharmaceutically acceptable excipient and the antibody of the invention. In these embodiments, the antibody can be further conjugated to an effector component. The effector component can be a label (e.g., a fluorescent label) or can be cytotoxic moiety (e.g., a radioisotope or a cytotoxic chemical) An exemplary cytotoxic chemical is auristatin. The antibodies in the pharmaceutical compositions can be whole antibodies or can antibody fragments. In some embodiments the immunoglobulin is a humanized antibody. An exemplary antibody TMEFF2#19 (ATCC Accession No. PTA-4127).

The invention further provides immunoassays using the immunoglobulins of the invention. These methods involve detecting a prostate cancer cell in a biological sample from a patient by contacting the biological sample with an antibody of the invention. The antibody is typically conjugated to a label such as fluorescent label.

The invention provides methods of inhibiting proliferation of a prostate cancer-associated cell. The method comprises contacting the cell with an antibody of the invention. In most embodiments, the cancer cell is in a patient, typically a human. The patient may be undergoing a therapeutic regimen to treat metastatic prostate cancer or may be suspected of having prostate cancer.

The invention also provides a method of treating prostate cancer with an antibody to TMEFF2, wherein said prostate cancer is selected from the group consisting of a primary prostate cancer, metastatic prostate cancer, locally advanced prostate cancer, androgen independent prostate cancer, prostate cancer that has been treated with neoadjuvant therapy, and prostate cancer that is refractory to treatment with neoadjuvant therapy.

DETAILED DESCRIPTION OF THE INVENTION

The present invention provides novel reagents and methods for treatment, diagnosis and prognosis for certain cancers using antibodies against TMEFF2. In particular, the present invention provides anti-TMEFF2 antibodies that are particularly useful as selective cytotoxic agents for TMEFF2 expressing cells. Without wishing to be bound by theory it is believed that the antibodies of the invention recognize a TMEFF2 epitope that effects an increased internalization and thus enhanced cell killing, when conjugated to a cytotoxic moiety. In addition, antibodies of the invention are useful because they recognize the non-glycosylated form of the protein. This is advantageous because antibodies that recognize the glycosylated portion of the protein may only recognize a subset of the expressed proteins. The invention is based, in part, on analysis of approximately 100 hybridoma supernatants. Epitope mapping of antibodies showing high affinity binding was carried out through competitive binding analyses. Using this methodology antibodies recognizing a number of individual epitopes were identified. The antibodies were then assessed for TMEFF2 dependent cell death in vitro. Using these methods antibodies that promoted significant cell death were identified.

DEFINITIONS

"Antibody" refers to a polypeptide comprising a framework region from an immunoglobulin gene, or fragments thereof, that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*. However, recombinant methods exist to chimerize and generate changed classes and effector functions.

An exemplary immunoglobulin (antibody) structural unit comprises a tetramer of four polypeptides. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce $F(ab')_2$, a dimer of Fab which itself is a light chain joined to VH-CH1 by a disulfide bond. The $F(ab')_2$ may be reduced under mild conditions to break the disulfide linkage in the hinge region, thereby converting the $F(ab')_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al. (1990) *Nature* 348:552-554).

For preparation of antibodies, e.g., recombinant, monoclonal, or polyclonal antibodies, many technique known in the art can be used (see, e.g., Kohler & Milstein (1975) *Nature* 256:495-497; Kozbor, et al. (1983) *Immunology Today* 4:72; Cole, et al., pp. 77-96 in *Monoclonal Antibodies and Cancer Therapy* (1985); Coligan (1991) *Current Protocols in Immunology*; Harlow & Lane (1988) *Antibodies: A Laboratory Manual*; and Goding (1986) *Monoclonal Antibodies: Principles and Practice* (2d ed.). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty, et al. (1990) Nature 348:552-554; Marks, et al. (1992) *Biotechnology* 10:779-783).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., "Epitope Mapping Protocols" in Morris (ed. 1996) *Methods in Molecular Biology*, Vol. 66.

The term "TMEFF2 protein" or "TMEFF2 polynucleotide" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleotides, to a nucleotide sequence of SEQ ID NO:1; (2) bind to antibodies, e.g., polyclonal antibodies, raised against an immunogen comprising an amino acid sequence encoded by a nucleotide sequence of SEQ ID NO: 1, and conservatively modified variants thereof; (3) specifically hybridize under stringent hybridization conditions to a nucleic acid sequence, or the complement thereof of SEQ ID NO: 1 and conservatively modified variants thereof or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of at least about 25, 50, 100, 200, or more amino acids, to an amino acid sequence of SEQ ID NO:2. A polynucleotide or polypeptide sequence is typically from a mammal including, but not limited to, primate, e.g., human; rodent, e.g., rat, mouse, hamster; cow, pig, horse, sheep, or other mammal. A "TMEFF2 polypeptide" and a "TMEFF2 polynucleotide," include both naturally occurring or recombinant forms. A number of different variants have been identified. See, e.g., LocusLink 23671.

A "full length" TMEFF2 protein or nucleic acid refers to a prostate cancer polypeptide or polynucleotide sequence, or a variant thereof, that contains all of the elements normally contained in one or more naturally occurring, wild type TMEFF2 polynucleotide or polypeptide sequences. For example, a full length TMEFF2 nucleic acid will typically comprise all of the exons that encode for the full length, naturally occurring protein. The "full length" may be prior to, or after, various stages of post-translation processing or splicing, including alternative splicing.

"Biological sample" as used herein is a sample of biological tissue or fluid that contains nucleic acids or polypeptides, e.g., of a TMEFF2 protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The term "prostate cancer stage" or grammatical equivalents thereof refer to the size of a cancer and whether it has spread beyond its original site. Prostate cancer is generally divided into four stages, from small and localized (stage 1), to spread into surrounding tissue (stage 3 and 4). If the cancer has spread to other parts of the body, this is known as secondary prostate cancer (or metastatic prostate cancer). There are two systems of prostate cancer staging the conventional system of the American Urological Association and a new system based on detection of prostate cancer by way of prostate serum antigen (PSA) tests. The new system known as the Tumor, Nodes and Metastasis System or TNM.

In the conventional AUA system stage A corresponds to clinically unsuspected prostate cancer. Stage B corresponds to a tumor confined to the prostate gland (localized). Stage C corresponds to a tumor outside prostate capsule, and stage D corresponds to metastasis into the pelvic lymph node. Stage D2 is distant metastatic cancer into distant lymph nodes, organs, soft tissue or bone.

In the TNM system stages include T1: The tumor is within the prostate gland and is too small to be detected during a rectal examination, but may be detected through tests such as PSA test. There are generally no symptoms. T2: The tumor is still within the prostate gland but is large enough to be felt during a digital rectal examination or show up on ultrasound. Often there are no symptoms. T3/T4: The cancer has spread beyond the prostate gland into the surrounding tissues. This is known as locally advanced prostate cancer. T1 and T2 tumors are known as early prostate cancer. T3 and T4 are known as locally advanced prostate cancer. If the lymph nodes, bones or other parts of the body are affected this is called secondary or metastatic cancer. "Locally advanced prostate cancer" refers to prostate cancer that shows some evidence of metastasis, or developing metastasis.

The term "neoadjuvant therapy" also known as "neoadjuvant androgen depravation therapy" refers to the treatment of prostate cancer by giving adjuvant hormone blocking drugs before surgery.

The terms "identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from about 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel, et al. (eds. 1995 and supplements) *Current Protocols in Molecular Biology*.

Preferred examples of algorithms that are suitable for determining percent sequence identity and sequence similarity include the BLAST and BLAST 2.0 algorithms, which are described in Altschul, et al. (1977) *Nuc. Acids Res.* 25:3389-3402 and Altschul, et al. (1990) *J. Mol. Biol.* 215:403-410. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul (1993) *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like (see, e.g., the American Type Culture Collection catalog.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton (1984) *Proteins*).

Macromolecular structures such as polypeptide structures can be described in terms of various levels of organization. For a general discussion of this organization, see, e.g., Alberts, et al. (1994) *Molecular Biology of the Cell* (3d ed.), and Cantor & Schimmel (1980) *Biophysical Chemistry Part I: The Conformation of Biological Macromolecules*. "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^3H$, $^{14}C$, $^{32}P$, $^{35}S$, or $^{125}I$. In some cases, particularly using antibodies against the proteins of the invention, the radioisotopes are used as toxic moieties, as described below. The labels may be incorporated into the TMEFF2 nucleic acids, proteins and antibodies at any position. A method known in the art for conjugating the antibody to the label may be employed, including those methods described by Hunter, et al. (1962) *Nature* 144:945; David, et al. (1974) *Biochemistry* 13:1014; Pain, et al. (1981) *J. Immunol. Meth.* 40:219; and Nygren (1982) *J. Histochem. and Cytochem.* 30:407. The lifetime of radiolabeled peptides or radiolabeled antibody compositions may extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard", e.g., beta radiation.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, e.g., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal'enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

Specific binding to an antibody under such conditions requires an antibody that is selected for its specificity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with TMEFF2 and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane (1988) *Antibodies: A Laboratory Manual* for a description of immunoassay formats and conditions that can be used to determine specific immunoreactivity).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney (1994) *Culture of Animal Cells: A Manual of Basic Technique* (3d ed.).

Expression of TMEFF2 Polypeptides from Nucleic Acids

Nucleic acids of the invention can be used to make a variety of expression vectors to express TMEFF2 polypeptides which can then be used to raise antibodies of the invention, as described below. Expression vectors and recombinant DNA technology are well known to those of skill in the art (see, e.g., Ausubel, supra, and Fernandez & Hoeffler (eds. 1999) *Gene Expression Systems*) and are used to express proteins. The expression vectors may be either self-replicating extrachromosomal vectors or vectors which integrate into a host genome. Generally, these expression vectors include transcriptional and translational regulatory nucleic acid operably linked to the nucleic acid encoding the TMEFF2 protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the TMEFF2 protein.

Numerous types of appropriate expression vectors, and suitable regulatory sequences are known in the art for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, an expression vector may comprise additional elements. For example, the expression vector may have two replication systems, thus allowing it to be maintained in two organisms, e.g., in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art (e.g., Fernandez & Hoeffler, supra).

In addition, in a preferred embodiment, the expression vector contains a selectable marker gene to allow the selection of transformed host cells. Selection genes are well known in the art and will vary with the host cell used.

The TMEFF2 proteins of the present invention are produced by culturing a host cell transformed with an expression vector containing nucleic acid encoding a TMEFF2 protein, under the appropriate conditions to induce or cause expression of the TMEFF2 protein. Conditions appropriate for TMEFF2 protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, Neurospora, CHO, COS, HeLa cells, HUVEC (human umbilical vein endothelial cells), THP1 cells (a macrophage cell line) and various other human cells and cell lines.

In a preferred embodiment, the TMEFF2 proteins are expressed in mammalian cells. Mammalian expression systems are also known in the art, and include retroviral and adenoviral systems. One expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter (see, e.g., Fernandez & Hoeffler, supra). Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, TMEFF2 proteins are expressed in bacterial systems. Bacterial expression systems are well known in the art. Promoters from bacteriophage may also be used and are known in the art. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the TMEFF2 protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others (e.g., Fernandez & Hoeffler, supra). The bacterial expression vectors are transformed into bacterial host cells using techniques well known in the art, such as calcium chloride treatment, electroporation, and others.

In one embodiment, TMEFF2 polypeptides are produced in insect cells. Expression vectors for the transformation of insect cells, and in particular, baculovirus-based expression vectors, are well known in the art.

TMEFF2 polypeptides can also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactic, Pichia guillerimondii* and *P. pastoris, Schizosaccharomyces pombe*, and *Yarrowia lipolytica*.

The TMEFF2 polypeptides may also be made as a fusion protein, using techniques well known in the art. Thus, e.g., for the creation of monoclonal antibodies, if the desired epitope is small, the TMEFF2 protein may be fused to a carrier protein to form an immunogen. Alternatively, the TMEFF2 protein may be made as a fusion protein to increase expression, or for other reasons. For example, when the TMEFF2 protein is a TMEFF2 peptide, the nucleic acid encoding the peptide may be linked to other nucleic acid for expression purposes.

The TMEFF2 polypeptides are typically purified or isolated after expression. TMEFF2 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the TMEFF2 protein may be purified using a standard anti-TMEFF2 protein antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the TMEFF2 protein. In some instances no purification will be necessary.

One of skill will recognize that the expressed protein need not have the wild-type TMEFF2 sequence but may be derivative or variant as compared to the wild-type sequence. These variants typically fall into one or more of three classes: substitutional, insertional or deletional variants. These variants ordinarily are prepared by site specific mutagenesis of nucleotides in the DNA encoding the protein, using cassette or PCR mutagenesis or other techniques well known in the art, to produce DNA encoding the variant, and thereafter expressing the DNA in recombinant cell culture as outlined above. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the TMEFF2 protein amino acid sequence. The variants typically exhibit the same qualitative biological activity as the naturally occurring analogue, although variants can also be selected which have modified characteristics as will be more fully outlined below.

TMEFF2 polypeptides of the present invention may also be modified in a way to form chimeric molecules comprising a TMEFF2 polypeptide fused to another, heterologous polypeptide or amino acid sequence. In one embodiment, such a chimeric molecule comprises a fusion of the TMEFF2 polypeptide with a tag polypeptide which provides an epitope to which an anti-tag antibody can selectively bind. The epitope tag is generally placed at the amino- or carboxyl-terminus of the TMEFF2 polypeptide. The presence of such epitope-tagged forms of a TMEFF2 polypeptide can be detected using an antibody against the tag polypeptide. Also, provision of the epitope tag enables the TMEFF2 polypeptide to be readily purified by affinity purification using an anti-tag antibody or another type of affinity matrix that binds to the epitope tag. In an alternative embodiment, the chimeric molecule may comprise a fusion of a TMEFF2 polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field, et al (1988) *Mol. Cell. Biol.* 8:2159-2165); the c-myc tag and the 8F9, 3C7, 6E10, G4, B7 and 9E10 antibodies thereto (Evan, et al. (1985) *Molecular and Cellular Biology* 5:3610-3616); and the Herpes Simplex virus glycoprotein D (gD) tag and its antibody (Paborsky, et al. (1990) *Protein Engineering* 3(6):547-553). Other tag polypeptides include the FLAG-peptide (Hopp, et al. (1988) *BioTechnology* 6:1204-1210); the KT3 epitope peptide (Martin, et al. (1992) *Science* 255:192-194); tubulin epitope peptide (Skinner, et al. (1991) *J. Biol. Chem.* 266:15163-15166); and the T7 gene 10 protein peptide tag (Lutz-Freyermuth, et al. (1990) *Proc. Natl. Acad. Sci. USA* 87:6393-6397).

Antibodies to Cancer Proteins

Once the TMEFF2 protein is produced, it is used to generate antibodies, e.g. for immunotherapy or immunodiagnosis. As noted above, the antibodies of the invention recognize the same epitope as that recognized by TMEFF2#19 (ATCC Accession No. PTA-4127). The ability of a particular antibody to recognize the same epitope as another antibody is typically determined by the ability of one antibody to competitively inhibit binding of the second antibody to the antigen. Many of a number of competitive binding assays can be used to measure competition between two antibodies to the same antigen. An exemplary assay is a Biacore™ assay as described in the Examples, below. Briefly in these assays, binding sites can be mapped in structural terms by testing the ability of interactants, e.g. different antibodies, to inhibit the binding of another. Injecting two consecutive antibody samples in sufficient concentration can identify pairs of competing antibodies for the same binding epitope. The antibody samples should have the potential to reach a significant saturation with each injection. The net binding of the second antibody injection is indicative for binding epitope analysis. Two response levels can be used to describe the boundaries of perfect competition versus non-competing binding due to distinct epitopes. The relative amount of binding response of the second antibody injection relative to the binding of identical and distinct binding epitopes determines the degree of epitope overlap.

Other conventional immunoassays known in the art can be used in the present invention. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Tables 1-2, fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (pp. 59-103 in Goding (1986) *Monoclonal Antibodies: Principles and Practice*). Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for a TMEFF2 protein, the other one is for any other prostate cancer antigen. Alternatively, tetramer-type technology may create multivalent reagents.

In a preferred embodiment, the antibodies to TMEFF2 protein are capable of reducing or eliminating prostate cancer cells. That is, the addition of anti-TMEFF2 antibodies (either polyclonal or preferably monoclonal) to prostate cancer tissue (or cells containing TMEFF2) may reduce or eliminate the prostate cancer. Generally, at least a 25% decrease in activity, growth, size or the like is preferred, with at least about 50% being particularly preferred and about a 95-100% decrease being especially preferred.

In a preferred embodiment the antibodies to the TMEFF2 proteins are humanized antibodies (e.g., Xenerex Biosciences, Medarex, Inc., Abgenix, Inc., Protein Design Labs, Inc.) Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, selectivity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones, et al. (1986) *Nature* 321:522-525; Riechmann, et al. (1988) *Nature* 332:323-329; and Presta (1992) *Curr. Op. Struct. Biol.* 2:593-596). Humanization can be essentially performed following the method of Winter and co-workers (Jones, et al. (1986) *Nature* 321:522-525; Riechmann, et al. (1988) *Nature* 332:323-327; Verhoeyen, et al. (1988) *Science* 239:1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom & Winter (1991) *J. Mol. Biol.* 227:381; Marks, et al. (1991) *J. Mol. Biol.* 222:581). The techniques of Cole, et al. and Boerner, et al. are also available for the preparation of human monoclonal antibodies (p. 77 in Cole, et al. (1985) *Monoclonal Antibodies and Cancer Therapy*; and Boerner, et al. (1991) *J. Immunol.* 147(1):86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks, et al. (1992) *Bio/Technology* 10:779-783; Lonberg, et al. (1994) *Nature* 368:856-859; Morrison (1994) *Nature* 368:812-13; Fishwild, et al. (1996) *Nature Biotechnology* 14:845-51; Neuberger (1996) Nature *Biotechnology* 14:826; and Lonberg & Huszar (1995) *Intern. Rev. Immunol.* 13:65-93.

By immunotherapy is meant treatment of prostate cancer with an antibody raised against TMEFF2 proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen, leading to an immune response.

In some embodiments, the antibody is conjugated to an effector moiety. The effector moiety can be any number of molecules, including labeling moieties such as radioactive labels or fluorescent labels, or can be a therapeutic moiety. In one aspect the therapeutic moiety is a small molecule that modulates the activity of the TMEFF2 protein. In another aspect the therapeutic moiety modulates the activity of molecules associated with or in close proximity to the TMEFF2 protein.

In other embodiments, the therapeutic moiety is a cytotoxic agent. In this method, targeting the cytotoxic agent to prostate cancer tissue or cells, results in a reduction in the number of afflicted cells, thereby reducing symptoms associated with prostate cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies raised against prostate cancer proteins, or binding of a radionuclide to a chelating agent that has been covalently attached to the antibody. Targeting the therapeutic moiety to transmembrane prostate cancer proteins not only serves to increase the local concentration of therapeutic moiety in the prostate cancer afflicted area, but also serves to reduce deleterious side effects that may be associated with the therapeutic moiety.

Binding Affinity of Antibodies of the Invention

Binding affinity for a target antigen is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is <1 µM, preferably <100 nM, and most preferably <0.1 nM. Antibody molecules will typically have a $K_D$ in the lower ranges. $K_D=[\text{Ab-Ag}]/[\text{Ab}][\text{Ag}]$ where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds.

The antibodies of the invention specifically bind to TMEFF2 proteins. By "specifically bind" herein is meant that the antibodies bind to the protein with a $K_D$ of at least about 0.1 mM, more usually at least about 1 µM, preferably at least about 0.1 µM or better, and most preferably, 0.01 µM or better.

Immunoassays

The antibodies of the invention can be used to detect TMEFF2 or TMEFF2 expressing cells using any of a number of well recognized immunological binding assays (see, e.g., U.S. Pat. Nos. 4,366,241; 4,376,110; 4,517,288; and 4,837,168). For a review of the general immunoassays, see also Asai (ed. 1993) *Methods in Cell Biology* Vol. 37, Academic Press, New York; Stites & Terr (eds. 1991) *Basic and Clinical Immunology* 7th Ed.

Thus, the present invention provides methods of detecting cells that express TMEFF2. In one method, a biopsy is performed on the subject and the collected tissue is tested in vitro. The tissue or cells from the tissue is then contacted, with an anti-TMEFF2 antibody of the invention. Any immune complexes which result indicate the presence of a TMEFF2 protein in the biopsied sample. To facilitate such detection, the antibody can be radiolabeled or coupled to an effector molecule which is a detectable label, such as a radiolabel. In another method, the cells can be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

TMEFF2 proteins can also be detected using standard immunoassay methods and the antibodies of the invention. Standard methods include, for example, radioimmunoassay, sandwich immunoassays (including ELISA), immunofluorescence assays, Western blot, affinity chromatography (affinity ligand bound to a solid phase), and in situ detection with labeled antibodies.

Administration of Pharmaceutical and Vaccine Compositions

The antibodies of the invention can be formulated in pharmaceutical compositions. Thus, the invention also provide methods and compositions for administering a therapeutically effective dose of an anti-TMEFF2 antibody. The exact dose will depend on the purpose of the treatment, and will be ascertainable by one skilled in the art using known techniques. See, e.g., Ansel, et al. (1999) *Pharmaceutical Dosage Forms and Drug Delivery*; Lieberman (1992) *Pharmaceutical Dosage Forms* (vols. 1-3), Dekker, ISBN 0824770846, 082476918X, 0824712692, 0824716981; Lloyd (1999) *The Art, Science and Technology of Pharmaceutical Compounding* Amer. Pharm. Assn.; and Pickar (1999) Dosage Calculations Thomson. Adjustments for cancer degradation, systemic versus localized delivery, and rate of new protein synthesis, as well as the age, body weight, general health, sex, diet, time of administration, drug interaction and the severity of the condition may be necessary, and will be ascertainable with routine experimentation by those skilled in the art. U.S. Ser. No. 09/687,576 further discloses the use of compositions and methods of diagnosis and treatment in prostate cancer is hereby expressly incorporated by reference.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The administration of the antibodies of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise an antibody of the invention in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody of the invention dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., (1980) *Remington's Pharmaceutical Science* (18th ed.); and Hardman, et al. (eds. 2001) *Goodman & Gilman: The Pharmacological Basis of Therapeutics*).

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., *Remington's Pharmaceutical Science* and *Goodman and Gilman: The Pharmacological Basis of Therapeutics*, supra.

The compositions containing antibodies of the invention can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer.

It will be appreciated that the present prostate cancer protein-modulating compounds can be administered alone or in combination with additional prostate cancer modulating compounds or with other therapeutic agent, e.g., other anti-cancer agents or treatments.

In some embodiments, the antibodies of the invention can be used to prepare targeted liposomes for delivery of a desired therapeutic composition (e.g., anti-cancer agents) to a target cell (e.g., a prostate cancer cell). The preparation and use of immunoliposomes for targeted delivery of antitumor drugs is reviewed in Mastrobattista, et al. (1999) *Advanced Drug Delivery Reviews* 40:103-127.

Liposomes are vesicular structures based on lipid bilayers. They can be as small as 20 nm and as large as 10 μm in diameter. They can be unilamellar (only one bilayer surrounds an aqueous core) or multilamellar (several bilayers concentrically oriented around an aqueous core). The liposomes of the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Targeting of liposomes using a variety of targeting agents (e.g., monoclonal antibodies of the invention) is well known in the art. See, e.g., U.S. Pat. Nos. 4,957,773 and 4,603,044). Standard methods for coupling targeting agents to liposomes can be used. Antibody targeted liposomes can be constructed using, for instance, liposomes which incorporate protein A. See, Renneisen, et al. (1990) *J. Biol. Chem.* 265:16337-16342; and Leonetti, et al. (1990) *Proc. Natl. Acad. Sci. USA* 87:2448-2451.

A variety of methods are available for preparing liposomes, as described in, e.g., Szoka, et al. (1980) *Ann. Rev. Biophys. Bioeng.* 9:467; U.S. Pat. Nos. 4,235,871; 4,501,728; and 4,837,028. One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component (antibody) and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, and TMEFF2-specific antibodies of the invention. A therapeutic product may include sterile saline or another pharmaceutically acceptable emulsion and suspension base.

In addition, the kits may include instructional materials containing directions (e.g., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Approximately 12 anti-TMEFF2 hybridoma supernatants were selected from an initial pool of roughly one hundred, based on off rates (kd) for binding to covalently immobilized TMEFF2-FLAG protein as measured by BIAcore™. Supernatants exhibiting the lowest dissociation rate constants were chosen for larger scale purification. The sequences of variable regions of antibodies TMEFF2 #19, TMEFF2 #10, TMEFF2 #18, TMEFF2 #20, TMEFF2 #21 are presented in Table 1. A kinetic evaluation was carried out on each purified antibody by measuring binding to TMEFF2-FLAG over a range of antigen concentrations. Affinity constants ($K_D$) were then determined using the global fitting procedure described in the BIAapplications Handbook Biacore AB, BIAapplications Handbook, version AB, 1998, Application Notes, Note 101 (June 1995); Daiss, et al. (1994) *Methods: A companion to Methods in Enzymology* Volume 6, p 143-156. In addition, pair-wise epitope mapping was carried out through a competitive binding analysis. This was accomplished by exposing the TMEFF2-FLAG surface to a saturating amount of one antibody sample and measuring the response level of a second injected antibody. Using this methodology antibodies recognizing a number of individual epitopes were selected for further study.

Each antibody of interest was covalently coupled to the synthetic toxin auristatin (*Int. J. Oncol.* 15:367-72 (1999)) (pAE), a dolastatin 10 derivative, and assessed for TMEFF2 dependent cell death in vitro. The cell death assay (*Proc. Nat'l Acad. Sci. USA* 93:8618-23 (1996)) was executed by first determining a cell density that exhibits linear cell growth over several days. Populations of dividing cells were then incubated with multiple concentrations of toxin-conjugated TMEFF2 antibodies (or a negative control) for one hour, followed by removal of the antibody and gentle washing. Four days later, cell viability was determined by using the Celltiter 96 assay (Promega). In this manner a prostate cancer cell line stably expressing TMEFF2 (PC3-TMEFF2), was compared with the parental cell line that does not (PC3).

Two antibodies corresponding to distinct epitopes, as determined by BIAcore, have been assessed for their ability to interfere with cell survival in vitro. One of these antibodies, TMEFF2 #19-pAE, appears to promote significant cell death in PC3-TMEFF2 cells, but not in the parental line. The other antibody, #21-pAE, also causes cell death, but with somewhat less potency than #19-pAE. A negative control antibody that does not recognize a cell surface marker in PC3 cells, TIB-pAE, does not affect cell survival in either cell line. Additionally, another prostate cancer line, LnCAP, which has been determined to express small amounts of surface TMEFF2, also displayed sensitivity to #19-pAE relative to TIB-pAE. These results show that #19-pAE is a potent and selective cytotoxic agent on TMEFF2 expressing cells.

TABLE 1

TMEFF2#19. Heavy chain variable region.
SEQ ID NO: 1
GATGTACAACTTCAGGAGTCAGGACCTGGCCTCGTGAAACCTTCTCAG
TCTCTGTCTCTCACCTGCTCTGTCACTGGCTACTCCATCACCAGTGGT
TATTACTGGAGCTGGATCCGGCAGTTTCCAGGAAACAAACTGGAATGG
ATGGGCTTCATAAGCTACGACGGTTCCAATAAGTATAATCCATCTCTC
AAAAATCGAATCTCCATCACTCGTGACACATCTGAGAACCAGTTTTTC
CTGAACTTGAGATCTGTGACTACTGAGGACACAGCAACATATTATTGT
GCAAGAGGTTTACGACGAGGGGACTATTCTATGGACTACTGGGGTCAA
GGAACCTCAGTCACCGTCTCCTCA SEQ ID NO: 2
DVQLQESGPGLVKPSQSLSLTCSVTGYSITSGYYWSWIRQFPGNKLEW
MGFISYDGSNKYNPSLKNRISITRDTSENQFFLNLRSVTTEDTATYYC
ARGLRRGDYSMDYWGQGTSVTVSS TMEFF2#19. Light chain variable region
SEQ ID NO: 3
GACATTGTGATGACCCAGTCTCAAAAATTCATGTCCACATCAGTAGGA
GACAGTGTCAGCATCACCTGCAAGGCCAGTCAGAATGTGGTTACAGCT
GTAGCCTGGTATCGACAGAAACCAGGACAATCTCCTAAACTACTGATT
TACTCGGCATCCAATCGGCACACTGGAGTCCCTGACCGCTTCACAGGC
AGTGGATCTGGGACAGATTTCACTCTCACCATCAACAATATGCAGTCT
GAAGACCTGGCAGATTATTTCTGCCAGCAATATAGCAGCTATCCGTTC
ACGTTCGGAGGGGGGACCAAGCTGGAAATAAAA SEQ ID NO: 4
DIVMTQSQKFMSTSVGDSVSITCKASQNVVTAVAWYRQKPGQSPKLLI
YSASNRHTGVPDRFTGSGSGTDFTLTINNMQSEDLADYFCQQYSSYPF
TFGGGTKLEIK TMEFF2#10. heavy chain variable region
SEQ ID NO: 5
GAAGTGAACCTGGTGGAGTCTGGGGGAGGCTTAGTGCAGCCTGGAGGG
TCCCTGAAACTCTCCTGTGCAACCTCTGGATTCACTTTCAGTGACTAT
TACATGTTCTGGATTCGCCAGACTCCAGAGAAGAGGCTGGAGTGGGTC
GCATACATTAGTAATGGTGGTGGTAATACCTATTATTCAGACACTGTA
AAGGGCCGATTCACCATCTCCAGAGACAATGCCAAGAACACCCTGTAC
CTCCAAATGAGCCGTCTGAAGTCTGAGGACACAGCCATGTATTACTGT
GCAAGACGGGATTACGACGAGGGGGGCTATGGACTACTGGGGTCAA
GGAACCTCAGTCACCGTCTCCTCA SEQ ID NO: 6
EVNLVESGGGLVQPGGSLKLSCATSGFTFSDYYMFWIRQTPEKRLEWV
AYISNGGGNTYYSDTVKGRFTISRDNAKNTLYLQMSRLKSEDTAMYYC
ARRGLRRGGAMDYWGQGTSVTVSS TMEFF2#10. Light chain variable region
SEQ ID NO: 7
GACATTGTTTGACCCAATCTCCAGCTTCTTTGGCTGTGTCTCTAGGG
CAGAGGGCCACCATCTCCTGCAAGGCCAGCCAAAGTGTTGATTACGGT
GGTTATGGTTATATAAACTGGTACCAACAGAAACCAGGACAGCCACCC
AAACTCCTCATCTATGCTGCATCCAATCTAGAATCTGGGATCCCAGCC
AGGTTTAGTGGCAGTGGGTCTGGGACAGATTTCACCCTCAACATCCAT
CCTGTGGAGGAGGAGGATGCTGCAGTCTATTACTGTCAACAAAGTTAT
GTGGATCCATTCACGTTCGGCTCGGGGACAAAGTTGGAAATAATC TABLE 1-continued SEQ ID NO: 8
DIVLTQSPASLAVSLGQRATISCKASQSVDYGGYGYINWYQQKPGQPP
KLLIYAASNLESGIPARFSGSGSGTDFTLNIHPVEEEDAAVYYCQQSY
VDPFTFGSGTKLEII TMEFF2#18. Heavy chain variable region
SEQ ID NO: 9
CAGATCCAGTTGGTGCAGTCTGGACCTGAGCTGAAGAAGCCTGGAGAG
ACAGTCAAGATCTCCTGCAAGGCTTCTGGGTATACCTTCACAAACTAT
GGAATGAGCTGGGTGAAGCAGGCTCCAGGAAAGGGTTTAAAGTGGATG
GGCTGGATAAACACCTACACTGGAGAGCCAACATATGCTGATGACTTC
AAGGGGCGGTTTGCCTTCTCTTTGGAAACCTCTGCCAGCACTGCCTAT
TTGCAGATCAACAACCTCAAAAATGAGGACACGGCTACATATTTCTGT
GGGGGTGATGCTTACTGGGGCCAAGGGACTCTGGTCACTGTCTCTGCA SEQ ID NO: 10
QIQLVQSGPELKKPGETVKISCKASGYTFTNYGMSWVKQAPGKGLKWM
GWINTYTGEPTYADDFKGRFAFSLETSASTAYLQINNLKNEDTATYFC
GGDAYWGQGTLVTVSA TMEFF2#18. Light chain variable region
SEQ ID NO: 11
GACATTGTGCTGACACAGTCTCCTGCTTCCTTAGCTGTATCTCTGGGG
CAGAGGGCCACCATCTCATGCAGGGCAGCAAAAGTGTCAGTACATCT
GGCTATAGTTATATGCACTGGTACCAACAGAAACCAGGACAGCCACCC
AAACTCCTCATCTATCTTGCATCCAACCTAGAATCTGGGGTCCCTGCC
AGGTTCAGTGGCAGTGGGTCTGGGACAGACTTCACCCTCAACATCCAT
CCTGTGGAGGAGGAGGATGCTGCAACCTATTACTGTCAGCACAGTAGG
GAGCTTCGGACGTTCGGTGGAGGCACCAAACTGGAAATCAAA SEQ ID NO: 12
DIVLTQSPASLAVSLGQRATISCRASKSVSTSGYSYMHWYQQKPGQPP
KLLIYLASNLESGVPARFSGSGSGTDFTLNIHPVEEEDAATYYCQHSR
ELRTFGGGTKLEIK TMEFF2#20. Heavy chain variable region
SEQ ID NO: 13
GAGATCCAGCTGCAGCAGTCTGGACCTGAGCTGATGAAGCCTGGGGCT
TCAGTGAAGATATCTTGCAAGGCTTCTACTTACTCATTCACTAGGTAC
TTCATGCACTGGGTGAAGCAGAGCCATGGAGAGAGCCTTGAGTGGATT
GGATATATTGATCCTTTCAATGGTGGTACTGGCTACAATCAGAAATTC
AAGGGCAAGGCCACATTGACTGTAGACAAATCTTCCAGCACAGCCTAC
ATGCATCTCAGCAGCCTGACATCTGAGGACTCTGCAGTCTATTACTGT
GTAACGTATGGCTCCGACTACTTTGACTATTGGGGCCAAGGCACCACT
CTCACAGTCTCCTCA SEQ ID NO: 14
EIQLQQSGPELMKPGASVKISCKASTYSFTRYFMHWVKQSHGESLEWI
GYIDPFNGGTGYNQKFKGKATLTVDKSSSTAYMHLSSLTSEDSAVYYC
VTYGSDYFDYWGQGTTLTVSS TMEFF2#20. Light chain variable region
SEQ ID NO: 15
GACATTGTGATGACCCAGCCACAAAAATTCATGTCCACGTCTGTAGGC
GACAGGGTCAGTGTCACCTGCAAGGCCAGTCAGAATGTGGAAACTGAT
GTAGTCTGGTATCAACAGAAACCTGGGCAACCACCTAAAGCACTGATT
TACTCGGCATCCTACCGGCACAGTGGAGTCCCTGATCGCTTCACAGGC
AGTGGATCTGGGACAAATTTCACTCTCACCATCAGCACTGTACAGTCT
GAAGACTTGGCAGAGTATTTCTGTCAGCAATATAACAACTATCCATTC
ACGTTCGGCTCGGGGACAAAGTTGGAAATAATA SEQ ID NO: 16
DIVMTQPQKFMSTSVGDRVSVTCKASQNVETDVVWYQQKPGQPPKALI
YSASYRHSGVPDRFTGSGSGTNFTLTISTVQSEDLAEYFCQQYNNYPF
TFGSGTKLEII TMEFF2#21. Heavy chain variable region
SEQ ID NO: 17
CAGATCCACTTGGTGCAGTCTGGACCTGAGCTGAAGAAGCCTGGAGAG
ACAGTCAAGATCTCCTGCAAGGCTTCTGGATATACCTTCACAAACTTT
GCAATGAACTGGGTGAAGCAGGCTCCAGGAAAGGGTTTCAAGTGGATG
GGCTGGATAAACACCTACACTGGAGAGCCAACATATGCTGATGACTTC
AAGGGACGGTTTGCCTTCTCTTTGGAACCTCTGTCAGTATTGCCTAT
TTGCAGATCAACAGCCTCAAAAATGAGGACACGGCTACATATTTCTGT
TCAAAATTTGACTACTGGGGCCAAGGCACCACTCTCACAGTCTCCTCA SEQ ID NO: 18
QIHLVQSGPELKKPGETVKISCKASGYTFTNFAMNWVKQAPGKGFKWM
GWINTYTGEPTYADDFKGRFAFSLETSVSIAYLQINSLKNEDTATYFC
SKFDYWGQGTTLTVSS TMEFF2#21. Light chain variable region
SEQ ID NO: 19
GACATCCAGATGACTCAGTCTCCAGCCTCCCTATATGCATCTGTGGGA
GAAACTGTCACCATCACATGTCGAGCAAGTGAGAATATTTACAGTTAT
TTAGCATGGTTTCAGCAGAAACAGGGAAAATCTCCTCACCTCCTGGTC
TATAATGCAAAAACCTTAGCAGCAGGTGTGCCATCAAGGTTCAGTGGC
AGTGGATCAGGCACACAGTTTTCTCTGAAGATCACCAGCCTGCAGCCT
GAAGATTTTGGGAGTTATTACTGTCAACATCATTATGGTACTCCCACG
TGGACGTTCGGTGGAGGCACCAAGCTGGAAATCAAA SEQ ID NO: 20
DIQMTQSPASLYASVGETVTITCRASENTYSYLAWFQQKQGKSPHLLV
YNAKTLAAGVPSRFSGSGSGTQFSLKITSLQPEDFGSYYCQHHYGTPT
WTFGGGTKLEIK Relatively low amounts of the TMEFF2 protein are detectable on the cell surface of cancer cell lines, as assessed by FACS analysis using the TMEFF2 #19 antibody. Thus, the effectiveness of the toxin-conjugated #19 antibody at killing cells specifically expressing this target was surprising. However, experiments designed to assess the ability of specific antibody:target combinations to be internalized has generated novel data that explains the efficiency of the toxin-conjugated anti TMEFF2 antibodies at killing. It has become apparent that this particular target protein shows an incredibly high rate of internalization. In these internalization experiments, cells expressing TMEFF2 are incubated at different temperatures, and for different lengths of time, in the presence of anti-TMEFF2 antibody. After incubation with anti-TMEFF2 antibody for 1 hour at 4° C., the cells are washed and further incubated with a fluorescently labeled anti-mouse antibody. By fluorescent microscopy a low level of specific antibody binding to the TMEFF2 at the cell surface is observed. In contrast, when cells are incubated at 37° C. for 1 hour, a temperature that allows for protein trafficking and internalization, and are then subjected to permeabilization and staining with the fluorescently labeled anti-mouse antibody, the majority of the fluorescence is detected within the cells. Such data indicates that the specific antibody:target combination has been internalized—a result that is further confirmed by subjecting the cells to an acid-stripping step prior to the detection step. The acid stripping removes all protein still present at the cell surface leaving behind only the internalized antibody:target proteins. In contrast to other antibody:target combinations such as herceptin:Her2 and anti-ephrinA3:ephrinA3, these experiments have shown that the TMEFF2 protein, as recognized by the specific anti-TMEFF2 antibodies, is internalized at a very rapid rate and also that almost complete internalization of the cell surface protein is observed within the 1 hour period. These data, showing the surprisingly efficient internalization of TMEFF2 account for the efficiency of the toxin-conjugated anti-TMEFF2 antibodies at killing.

Example 2

Using standard techniques as described above, humanized TMEFF2#19 antibodies were generated. The sequences of four humanized heavy chain variable regions and three humanized light chain variable regions are presented in Table 2. The heavy and light chain variable regions may be used to combine into binding sites, and among the tested combinations, retain binding affinity. These antibodies can be used in in vivo mouse models to inhibit growth of tumor cells in vivo.

TABLE 2

VH 1.0 DNA
SEQ ID NO: 21
GATGTACAACTTCAGGAGTCAGGACCTGGCCTCGTGAAACCTTCTGAG
ACCCTGTCTCTCACCTGCGCAGTCACTGGCTACTCCATCACCAGTGGT
TATTACTGGAGCTGGATCCGGCAGTTTCCAGGAAAGAAACTGGAATGG
ATGGGCTTCATAAGCTACGACGGTTCCAATAAGTATAATCCATCTCTC
AAAAATCGAATCTCCATCACTCGTGACACATCTGAGAACCAGTTTTTC
CTGAAGTTGTCTTCTGTGACTGCAGCAGACACAGCAACATATTATTGT
GCAAGAGGTTTACGACGAGGGGACTATTCTATGGACTACTGGGGTCAA
GGAACCCTGGTCACCGTCTCCTCA

VH 1.0 AMINO ACIDS
SEQ ID NO: 22
DVQLQESGPGLVKPSETLSLTCAVTGYSITSGYYWSWIRQFPGKKLEW
MGFISYDGSNKYNPSLKNRISITRDTSENQFFLKLSSVTAADTATYYC
ARGLRRGDYSMDYWGQGTLVTVSS

VH 2.0 DNA
SEQ ID NO: 23
GATGTACAACTTCAGGAGTCAGGACCTGGCCTCGTGAAACCTTCTGAG
ACCCTGTCTCTCACCTGCGCAGTCACTGGCTACTCCATCACCAGTGGT
TATTACTGGAGCTGGATCCGGCAGCCTCCAGGAAAGGGCCTGGAATGG
ATGGGCTTCATAAGCTACGACGGTTCCAATAAGTATAATCCATCTCTC
AAAAATCGAATCTCCATCACTCGTGACACATCTGAGAACCAGTTTTTC
CTGAAGTTGTCTTCTGTGACTGCAGCAGACACAGCAGTCTATTATTGT
GCAAGAGGTTTACGACGAGGGGACTATTCTATGGACTACTGGGGTCAA
GGAACCCTGGTCACCGTCTCCTCA

VH 2.0 AMINO ACIDS
SEQ ID NO: 24
DVQLQESGPGLVKPSETLSLTCAVTGYSITSGYYWSWIRQPPGKGLEW
MGFISYDGSNKYNPSLKNRISITRDTSENQFFLKLSSVTAADTAVYYC
ARGLRRGDYSMDYWGQGTLVTVSS

VH3.0 DNA
SEQ ID NO: 25
GATGTACAACTTCAGGAGTCAGGACCTGGCCTCGTGAAACCTTCTGAG
ACCCTGTCTCTCACCTGCGCAGTCAGCGGCTACTCCATCACCAGTGGT
TATTACTGGAGCTGGATCCGGCAGCCTCCAGGAAAGGGCCTGGAATGG
ATGGGCTTCATAAGCTACGACGGTTCCAATAAGTATAATCCATCTCTC
AAAAATCGAATCACCATCTCCCGTGACACATCTAAGAACCAGTTTTCC
CTGAAGTTGTCTTCTGTGACTGCAGCAGACACAGCAGTCTATTATTGT
GCAAGAGGTTTACGACGAGGGGACTATTCTATGGACTACTGGGGTCAA
GGAACCCTGGTCACCGTCTCCTCA

VH 3.0 AMINO ACIDS
SEQ ID NO: 26
DVQLQESGPGLVKPSETLSLTCAVSGYSITSGYYWSWIRQPPGKGLEW
MGFISYDGSNKYNPSLKNRITISRDTSKNQFSLKLSSVTAADTAVYYC
ARGLRRGDYSMDYWGQGTLVTVSS

VH 4.0 DNA
SEQ ID NO: 27
GATGTACAACTTCAGGAGTCAGGACCTGGCCTCGTGAAACCTTCTGAG
ACCCTGTCTCTCACCTGCGCAGTCAGCGGCTACTCCATCACCAGTGGT
TATTACTGGAGCTGGATCCGGCAGTTTCCAGGAAAGAAACTGGAATGG
ATGGGCTTCATAAGCTACGACGGTTCCAATAAGTATAATCCATCTCTC
AAAAATCGAATCACCATCTCCCGTGACACATCTAAGAACCAGTTTTCC
CTGAAGTTGTCTTCTGTGACTGCAGCAGACACAGCAACATATTATTGT
GCAAGAGGTTTACGACGAGGGGACTATTCTATGGACTACTGGGGTCAA
GGAACCCTGGTCACCGTCTCCTCA

VH 4.0 AMINO ACIDS
SEQ ID NO: 28
DVQLQESGPGLVKPSETLSLTCAVSGYSITSGYYWSWIRQFPGKKLEW
MGFISYDGSNKYNPSLKNRITISRDTSKNQFSLKLSSVTAADTATYYC
ARGLRRGDYSMDYWGQGTLVTVSS

VL 1.0 DNA
SEQ ID NO: 29
GACATTCAGATGACCCAGTCTCAATCTAGTATGTCCACATCAGTAGGA
GACCGAGTCACCATCACCTGCAAGGCCAGTCAGAATGTGGTTACAGCT
GTAGCCTGGTATCGACAGAAACCAGGAAAGTCTCCTAAACTACTGATT
TACTCGGCATCCAATCGGCACACTGGAGTCCCTAGTCGCTTCTCTGGC
AGTGGATCTGGGACAGATTTCACTCTCACCATCTCTAGCATGCAGCCT
GAAGACTTCGCAGATTATTTCTGCCAGCAATATAGCAGCTATCCGTTC
ACGTTCGGAGGGGGGACCAAGCTCGAGATCAAACGG

TABLE 2-continued

VL 1.0 AMINO ACIDS
SEQ ID NO: 30
DIQMTQSQSSMSTSVGDRVTITCKASQNVVTAVAWYRQKPGKSPKLLI
YSASNRHTGVPSRFSGSGSGTDFTLTISSMQPEDFADYFCQQYSSYPF
TFGGGTKLEIKR

VL 2.0 DNA
SEQ ID NO: 31
GACATTCAGATGACCCAGTCTCCATCTAGTCTGTCCGCTTCAGTAGGA
GACCGAGTCACCATCACCTGCAAGGCCAGTCAGAATGTGGTTACAGCT
GTAGCCTGGTATCGACAGAAACCAGGAAAGTCTCCTAAACTACTGATT
TACTCGGCATCCAATCGGCACACTGGAGTCCCTAGTCGCTTCTCTGGC
AGTGGATCTGGGACAGATTTCACTCTCACCATCTCTAGCCTGCAGCCT
GAAGACTTCGCAGATTATTTCTGCCAGCAATATAGCAGCTATCCGTTC
ACGTTCGGAGGGGGGACCAAGGTCGAGATCAAACGG

VL 2.0 AMINO ACIDS
SEQ ID NO: 32
DIQMTQSPSSLSASVGDRVTITCKASQNVVTAVAWYRQKPGKSPKLLI
YSASNRHTGVPSRFSGSGSGTDFTLTISSLQPEDFADYFCQQYSSYPF
TFGGGTKVEIKR

VL 3.0 DNA
SEQ ID NO: 33
GACATTCAGATGACCCAGTCTCCATCTAGTCTGTCCGCTTCAGTAGGA
GACCGAGTCACCATCACCTGCAAGGCCAGTCAGAATGTGGTTACAGCT
GTAGCCTGGTATCAGCAGAAACCAGGAAAGGCCCCTAAACTACTGATT
TACTCGGCATCCAATCGGCACACTGGAGTCCCTAGTCGCTTCTCTGGC
AGTGGATCTGGGACAGATTTCACTCTCACCATCTCTAGCCTGCAGCCT
GAAGACTTCGCAACCTATTATTGCCAGCAATATAGCAGCTATCCGTTC
ACGTTCGGAGGGGGGACCAAGGTCGAGATCAAACGG

VL 3.0 AMINO ACIDS
SEQ ID NO: 34
DIQMTQSPSSLSASVGDRVTITCKASQNVVTAVAWYQQKPGKAPKLLI
YSASNRHTGVPSRFSGSGSGTDFTLTISSLQPEDFATYYCQQYSSYPF
TFGGGTKVEIKR

Example 3

Auristatin E Conjugated Anti-TMEFF2 Antibodies Target and Kill Prostate Cancer Tumors In Vivo The TMEFF2 gene is highly and specifically expressed in clinical prostate cancer samples. To demonstrate that the protein product of the TMEFF2 gene is a therapeutic target for the treatment of prostate cancer, the human prostate cancer cell line LNCAP was modeled in SCID (severe combined immunodeficient) mice. Gene expression analysis shows that TMEFF2 is highly expressed in LNCAP cells grown on plastic in tissue culture and also when grown as xenograft tumors in SCID mice.

To determine the in vivo effects of toxin-conjugated anti-TMEFF2 antibodies (#19-pMMVCAE), LNCAP cells were grown as xenograft tumors in SCID mice. After the tumors reached a certain size (average of 100 mm$^3$), the animals were distributed into 3 groups and subjected to treatment with either a) control vehicle, b) #19-pMMVCAE, or c) isotype control-MMVCAE (an antibody that does not recognize molecules on the surface of LNCAP cells). Conjugated antibodies were used at 0.25 mg/kg of drug equivalent (~5 mg/kg of antibody-drug conjugate), and were administered at 4 day intervals. Tumor size was measured twice a week. Animal weight was monitored throughout the experiment and serum PSA (prostate-specific antigen) levels were measured at various time intervals during the experiment.

The results showed that treatment with #19-pMMVCAE significantly reduced LNCAP tumor growth. In fact, established LNCAP tumors regressed in size (to less than 100 mm$^3$), serum PSA (a surrogate marker for prostate tumor burden) levels significantly dropped (<10 ng/ml), while animal weight remained steady and animals appeared healthy. This is in contrast to mice that received either control vehicle or the isotype control-MMVCAE. The tumors in these mice grew rapidly and had to be sacrificed at days 50-60 post tumor implantation due to the large size of the tumors (>500 mm$^3$). In addition, the animals lost considerable amount of weight, appeared moribund and had significantly higher levels of serum PSA (>350 ng/ml). Treatment with humanized #19-pMMVCAE (see Example 2) of mice bearing LNCAP tumors elicited similar results as seen with the murine antibody, e.g., established tumors regressed, serum PSA levels dropped and animals appeared healthy.

These results indicate that TMEFF2 protein is a new therapeutic target for the treatment of prostate cancer and other prostatic diseases (such as benign prostatic hyperplasia—BPH) that exhibit TMEFF2 expression. In fact, anti-TMEFF2 treatment will allow for a more effective treatment of prostate cancer and BPH patients while reducing the need for surgery, radiation and chemotherapeutic treatment.

Example 4

Immunohistochemical Analysis of TMEFF2 in Clinical Samples Shows Significant Protein Expression in Prostate Cancer To determine how prevalent the TMEFF2 protein target is in prostate cancer patients, immunohistochemistry (IHC) was performed on clinical specimens derived from radical prostatectomies of patients that exhibited localized prostate cancer (Gleason grades 3-5). In addition, a small number of lymph node metastases of prostate cancer and advanced D2 stage prostate cancer samples were analyzed.

To perform IHC on these clinical specimens, a monoclonal antibody directed to TMEFF2 (clone #19) was used on tissue microarrays and individual slides of prostate cancer specimens. Tissue microarrays were generated by incorporating tissue core biopsies of 1.0 mm into medium-density tissue microarrays (Beecher Instruments, Silver Spring, Md.) employing the technique described by Kononen, et al. (1998) *Nature Med* 4:844-847). Hematoxylin and eosin stained template sections of the radical prostatectomy paraffin donor blocks were marked up for areas of nodular hyperplasia and cancer by a histopathologist. Using these sections as a guide, 1-2 cores of nodular hyperplasia adjacent to cancer (≦2 cm from the cancer) and 2-4 cores of cancer were sampled from the paraffin donor blocks of each of the radical prostatectomy specimens and incorporated directly into recipient array blocks. A core was included from each of the primary, secondary and tertiary Gleason patterns represented in the cancers. The normal prostate, lymph node metastases specimen, and D2 stage specimens were mounted as conventional tissue sections.

Immunohistochemical (IHC) staining for TMEFF2 was performed on routinely processed, paraffin-embedded tissue specimens. Four μm sections of these specimens were cut, mounted on Superfrost Plus adhesion slides (Lomb Scientific, Sydney, Australia), and heated in a convection oven at 75° C. for 2 hours to promote adherence to the slide. Paraffin-embedded pellets of LNCAP and PC-3 prostate cancer cell lines were used as positive and negative controls, respectively. Sections were de-waxed and rehydrated before unmasking in EDTA/Citrate buffer and were then stained with anti-TMEFF2 antibody. Anti-TMEFF2 signal was detected using DAKO EnVision Plus Labeled Polymer (DAKO Corporation, Carpinteria, Calif.) with liquid 3,3'-diaminobenzidine Plus (DAKO Corporation, Carpinteria, Calif.) as substrate. Counterstaining was performed with hematoxylin and Scott's bluing solution. All TMEFF2 immunostaining was cytoplasmic and the intensity of staining was graded on the density of cytoplasmic granules as negative, weak, moderate, or strong.

The results show that anti-TMEFF2 staining was restricted exclusively to the cytoplasm and membranes of prostatic epithelial cells with no nuclear or stromal staining. Benign prostatic tissue displayed some TMEFF2 protein expression with weak to moderate staining seen in normal prostate specimens and weak to moderate staining seen in the Benign Prostatic Hyperplasia (BPH samples). Expression in areas of hyperplasia adjacent to cancer also showed moderate staining in most of the cases examined. The prostate cancer cohort (n=241) displayed weak to strong staining in 176 cases, demonstrating that a large fraction of prostate cancer patients exhibit expression of TMEFF2. TMEFF2-positivity was also detected in 4/6 cases of locally advanced disease (D2 stage) and 3/5 lymph node metastatic lesions, indicating that expression of this target is retained in advanced stage disease.

Intensity of immunostaining for TMEFF2 protein in normal non-prostate body tissues was consistent with the levels of RNA expression detected in the transcript profiling. Only brain showed low levels of TMEFF2 expression. No expression was detected in the following normal tissues: bladder, cervix, small intestine, spinal cord, myometrium, pancreas, skin, colon, liver, heart, kidney, testes, lung, adrenal gland, skeletal muscle, spleen, and lymph node. This data confirms the prostate and prostate cancer specificity of TMEFF2.

These results, combined with the antibody-drug conjugate mediated killing of TMEFF2 expressing tumor cells, indicate that TMEFF2 is a good therapeutic target for the treatment of prostate cancer.

Example 5

Use of TMEFF2 Antibodies to Delay the Onset of Androgen-Independence of Prostate Cancer and/or to Treat Androgen-Independent Disease Prostate cancer is a hormone regulated disease that affects men in the later years of life. Untreated prostate cancer metastasizes to lymph nodes and bone in advanced cases. In such cases current treatment consists of antagonizing the androgenic growth-stimulus that feeds the tumor by chemical or surgical hormone-ablation therapy (Galbraith and Duchesne. (1997) *Eur. J. Cancer* 33:545-554). An unfortunate consequence of anti-androgen treatment is the development of androgen-independent cancer. Androgen regulated genes, such as the gene encoding prostate-specific antigen (PSA), are turned off with hormone-ablation therapy, but reappear when the tumor becomes androgen-independent (Akakura et al. (1993) *Cancer* 71:2782-2790).

To study the progression of androgen-dependent prostate cancer to androgen-independent prostate cancer the human CWR22 prostate cancer xenograft model was propagated in nude mice (see Pretlow, et al. (1993) *J. Natl. Cancer Inst.* 85:394-398). The CWR22 xenograft is androgen-dependent when grown in male Nude mice. Androgen-independent sublines can be derived by first establishing androgen-dependent tumors in male mice. The mice are then castrated to remove the primary source of growth stimulus (androgen), resulting in tumor regression. Within 3-4 months molecular events prompt the tumors to relapse and start growing as androgen-independent tumors. See, e.g., Nagabhushan, et al. (1996)

Cancer Res. 56:3042-3046; Amler, et al. (2000) *Cancer Res.* 60:6134-6141; and Bubendorf, et al. (1999) *J. Natl. Cancer Inst.* 91:1758-1764.

Using the CWR22 xenograft model we have previously monitored the gene expression changes that occur during the transition from androgen-dependence to androgen-independence (see WO02098358). Tumors were grown subcutaneously in male nude mice. Tumors were harvested at different times after castration. The time points ranged from 0 to 125 days post-castration. Castration resulted in tumor regression. At day 120 and thereafter, the tumors relapsed and started growing in the absence of androgen.

Gene expression profiling of the harvested tumors was accomplished using the Eos Hu03 oligonucleotide microarray (Affymetrix Eos Hu03). Our results identified several hundred genes that exhibited significant gene expression changes associated with androgen ablation therapy. Some genes were associated with the androgen-dependent growth phase of the CWR22 tumors (pre-castration and 1-5 days post-castration), some genes were associated with the androgen-withdrawal phase (10-82 days post castration, characterized by tumor regression and/or tumor growth stasis), and some genes were associated with the androgen-independent growth of CWR22 (greater than 120 days post castration). See WO02098358.

The gene encoding TMEFF2 showed high expression levels throughout such a whole androgen-withdrawal experiment. Highest expression levels were seen in the androgen-dependent CWR22 xenografts (confirmed by immunohistochemistry for the presence of TMEFF2 protein) and in the emerging androgen-independent CWR22 tumors (>120 days post-castration). Lower, but still significant expression was detected in tumors 10-82 days post castration (androgen-withdrawal phase).

To prevent androgen-independent prostate cancer, CWR22 tumor bearing mice are treated, post androgen-ablation therapy, with anti-TMEFF2 antibody conjugated to Auristatin E (#19-pMMVCAE). The objective is to show that post-castration treatment with #19-pMMVCAE during the androgen-withdrawal phase (10-82 days post castration) will result in a delay in the onset of androgen-independent CWR22 tumor growth. CWR22 tumors are grown in male immunodeficient mice for 2-3 weeks. The mice are then castrated to induce tumor regression and entry into the androgen-withdrawal phase. Twenty days post-castration the tumors are treated with #19-pMMVCAE as described in Example 3. A significant effect of #19-pMMVCAE would manifest itself in a delay in the onset of androgen-independence (e.g., 5 months or more post castration). This would suggest that patients with advanced stage prostate cancer, that are treated with androgen-ablation therapy, would greatly benefit from treatment with humanized #19-pMMVCAE. These patients would at the very least enjoy a longer survival period post androgen-ablation therapy and would possibly be cured of prostate cancer.

A non-significant effect in #19-pMMVCAE treatment may be due to several potential factors: (a) CWR22 xenograft tumors may be resistant to Auristatin E; (b) the tumor cells may not efficiently internalize #19-pMMVCAE during the androgen-withdrawal phase; or (c) TMEFF2 protein expression may be significantly decreased during the androgen-withdrawal phase. Modifications in treatment are available to address these issues.

To treat androgen-independent prostate cancer, CWR22 tumor bearing mice are treated at the time of onset of androgen-independence with #19-pMMVCAE. The objective is to show that post-castration treatment with #19-pMMVCAE during the emergence of androgen-independence (>120 days post castration) will result in regression of androgen-independent CWR22 tumors. CWR22 tumors are grown in male immunodeficient mice for 2-3 weeks. The mice are then castrated to induce tumor regression and entry into the androgen-withdrawal phase. Ten days after the tumors start growing in an androgen-independent manner, the tumors are treated with #19-pMMVCAE as described in Example 3. A significant effect of #19-pMMVCAE would manifest itself in regression of androgen-independent tumors. This would suggest that patients that were treated with androgen-ablation therapy and that suffered relapse in the form of androgen-independent tumor growth and metastasis would greatly benefit from treatment with humanized #19-pMMVCAE treatment. These patients, which currently do not have an alternative treatment, would at the very least enjoy a longer survival period after the emergence of androgen-independent prostate cancer and would possibly be cured of the disease.

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

All UniGene cluster identification numbers and accession numbers herein are for the GenBank sequence database and the sequences of the accession numbers are hereby expressly incorporated by reference. GenBank is known in the art, see, e.g., Benson, et al. (1998) *Nucleic Acids Research* 26:1-7. Sequences are also available in other databases, e.g., European Molecular Biology Laboratory (EMBL) and DNA Database of Japan (DDBJ).

What is claimed is:

1. An isolated antibody or antigen binding fragment that binds a TMEFF2 protein and competes for binding to said protein with TMEFF2#19 antibody, wherein the TMEFF2#19 antibody is produced by the hybridoma cell line deposited as ATCC Accession No: PTA-4127 and wherein the antibody or binding fragment comprises the complementary determining regions (CDRs) of SEQ ID NO: 28 which are present in a heavy chain variable region, and the CDRs of SEQ ID NO: 32 which are present in a light chain variable region.

2. The antibody of claim 1, wherein the TMEFF2 protein is on a prostate cancer cell.

3. The antibody of claim 2, wherein the prostate cancer cell is in a patient.

4. The antibody of claim 1, wherein the antigen binding fragment is a Fab or F(ab)$_2$ fragment.

5. The antibody of claim 1, wherein the antibody is humanized.

6. The antibody of claim 1, wherein the antibody is a monoclonal.

7. The antibody of claim 1, wherein the antibody is conjugated to a detectable label.

8. The antibody of claim 7, wherein the detectable label is a fluorescent label.

9. The antibody of claim 1, wherein the antibody is conjugated to an effector component selected from the group consisting of a toxin, a chemotherapeutic agent, and a radioisotope.

10. The antibody of claim 9, wherein the toxin is selected from the group consisting of diphtheria A, exotoxin A, ricin A, abrin A, curcin, crotin, phenomycin, neomycin, and auristatin.

11. The antibody of claim 10, wherein the toxin is auristatin.

12. The antibody of claim 1 comprising the heavy chain variable region selected from the group consisting of an amino acid sequence of SEQ ID NOs: 22, 24, and 28; and the light chain variable region selected from the group consisting of an amino acid sequence of SEQ ID NOs: 30 and 32.

13. The antibody of claim 12, wherein:
the heavy chain variable region comprises the amino acids of SEQ ID NO: 22 and the light chain variable region comprises the amino acids of SEQ ID NO: 30;
the heavy chain variable region comprises the amino acids of SEQ ID NO: 22 and the light chain variable region comprises the amino acids of SEQ ID NO: 32;
the heavy chain variable region comprises the amino acids of SEQ ID NO: 24 and the light chain variable region comprises the amino acids of SEQ ID NO: 30;
the heavy chain variable region comprises the amino acids of SEQ ID NO: 24 and the light chain variable region comprises the amino acids of SEQ ID NO: 32;
the heavy chain variable region comprises the amino acids of SEQ ID NO: 28 and the light chain variable region comprises the amino acids of SEQ ID NO: 30; or
the heavy chain variable region comprises the amino acids of SEQ ID NO: 28 and the light chain variable region comprises the amino acids of SEQ ID NO: 32.

14. The antibody of claim 1, wherein the antibody comprises a protein comprising the heavy chain variable region encoded by a nucleic acid sequence selected from the group consisting of SEQ ID NOs: 21, 23, and 27; and the light chain variable region encoded by a nucleic acid sequence selected from the group consisting of SEQ ID NOs: 29 and 31.

15. The antibody of claim 14, wherein:
the heavy chain variable region is encoded by the nucleic acid sequence of SEQ ID NO: 21 and the light chain variable region is encoded by the nucleic acid sequence of SEQ ID NO: 29;
the heavy chain variable region is encoded by the nucleic acid sequence of SEQ ID NO: 21 and the light chain variable region is encoded by the nucleic acid sequence of SEQ ID NO: 31;
the heavy chain variable region is encoded by the nucleic acid sequence of SEQ ID NO: 23 and the light chain variable region is encoded by the nucleic acid sequence of SEQ ID NO: 29;
the heavy chain variable region is encoded by the nucleic acid sequence of SEQ ID NO: 23 and the light chain variable region is encoded by the nucleic acid sequence of SEQ ID NO: 31;
the heavy chain variable region is encoded by the nucleic acid sequence of SEQ ID NO: 27 and the light chain variable region is encoded by the nucleic acid sequence of SEQ ID NO: 29; or
the heavy chain variable region is encoded by the nucleic acid sequence of SEQ ID NO: 27 and the light chain variable region is encoded by the nucleic acid sequence of SEQ ID NO: 31.

16. The antibody of claim 14, wherein the antibody is conjugated to a detectable label.

17. The antibody of claim 16, wherein the detectable label is a fluorescent label.

18. The antibody of claim 14, wherein the antibody is conjugated to an effector component selected from the group consisting of a toxin, a chemotherapeutic agent, and a radioisotope.

19. The antibody of claim 18, wherein the toxin is selected from the group consisting of diphtheria A, exotoxin A, ricin A, abrin A, curcin, crotin, phenomycin, neomycin, and auristatin.

20. The antibody of claim 19, wherein the toxin is auristatin.

21. A pharmaceutical composition comprising a pharmaceutically acceptable excipient and the antibody of any one of claims 1-20.

* * * * *